US010736603B2

(12) United States Patent
Messas et al.

(10) Patent No.: US 10,736,603 B2
(45) Date of Patent: Aug. 11, 2020

(54) METHOD AND APPARATUS FOR TREATING VALVULAR DISEASE

(71) Applicant: CARDIAWAVE, Paris (FR)

(72) Inventors: Emmanuel Messas, Paris (FR); Mathieu Pernot, Paris (FR); Mickael Tanter, Bagneux (FR); Olivier Villemain, Paris (FR)

(73) Assignee: CARDIAWAVE, Paris (FR)

( * ) Notice: Subject to any disclaimer, the term of this patent is extended or adjusted under 35 U.S.C. 154(b) by 399 days.

(21) Appl. No.: 15/557,455

(22) PCT Filed: Apr. 1, 2016

(86) PCT No.: PCT/IB2016/000523
§ 371 (c)(1),
(2) Date: Sep. 11, 2017

(87) PCT Pub. No.: WO2016/156989
PCT Pub. Date: Oct. 6, 2016

(65) Prior Publication Data
US 2018/0064412 A1    Mar. 8, 2018

Related U.S. Application Data

(60) Provisional application No. 62/142,096, filed on Apr. 2, 2015.

(51) Int. Cl.
*A61B 8/06* (2006.01)
*A61B 8/08* (2006.01)
(Continued)

(52) U.S. Cl.
CPC .................. *A61B 8/06* (2013.01); *A61B 8/04* (2013.01); *A61B 8/0883* (2013.01); *A61B 8/12* (2013.01);
(Continued)

(58) Field of Classification Search
CPC .......... A61B 8/06; A61B 8/0883; A61B 8/12; A61B 8/04; A61B 2017/00398;
(Continued)

(56) References Cited

U.S. PATENT DOCUMENTS 4,655,205 A    4/1987  Hepp et al.
4,693,247 A *  9/1987  Brisson ................ A61B 17/225
                                                    601/4
(Continued)

FOREIGN PATENT DOCUMENTS

CN    101754784 A    6/2010
CN    101874915 A    11/2010
(Continued)

OTHER PUBLICATIONS

Otsuka ["In Vitro Ablation of Cardiac Valves Using High-Intensity Focused Ultrasound" Ultrasound in Med. & Biol., vol. 31, No. 1, pp. 109-114, 2005]. (Year: 2005).*
(Continued)

*Primary Examiner* — Oommen Jacob
(74) *Attorney, Agent, or Firm* — Baker & Hostetler LLP

(57) ABSTRACT

An apparatus for treating or preventing a valvular disease comprises: a ultrasound probe located externally to a heart of patient, able to produce ultrasound waves focused inside the heart and suitable to generate, at a focal spot, a pressure sufficient to result in cavitation, an imaging device for mapping in real time a treatment region of a cardiac valve of the patient, the treatment region comprising at least one leaflet of the cardiac valve, a controller configured for driving the ultrasound probe to emit a sequence of focused ultrasound waves, the controller being further configured for steering the focused ultrasound waves so as to scan the entire treatment region to soften the tissues of the treatment region. A method for treating or preventing valvular disease, carried out using the apparatus is also provided.

32 Claims, 16 Drawing Sheets

(51) Int. Cl.

| | |
|---|---|
| *A61N 7/02* | (2006.01) |
| *A61B 8/12* | (2006.01) |
| *A61B 8/04* | (2006.01) |
| *A61N 7/00* | (2006.01) |
| *A61B 34/20* | (2016.01) |
| *A61B 34/30* | (2016.01) |
| *A61B 90/00* | (2016.01) |
| *A61B 5/00* | (2006.01) |
| *A61B 8/00* | (2006.01) |
| *A61B 17/00* | (2006.01) |
| *A61B 5/0215* | (2006.01) |
| *A61F 2/24* | (2006.01) |

(52) U.S. Cl.
CPC .............. *A61N 7/02* (2013.01); *A61B 5/0053* (2013.01); *A61B 5/0215* (2013.01); *A61B 8/445* (2013.01); *A61B 8/4483* (2013.01); *A61B 8/485* (2013.01); *A61B 8/488* (2013.01); *A61B 34/30* (2016.02); *A61B 2017/00398* (2013.01); *A61B 2034/2063* (2016.02); *A61B 2034/2065* (2016.02); *A61B 2090/374* (2016.02); *A61B 2090/376* (2016.02); *A61B 2090/378* (2016.02); *A61B 2090/3782* (2016.02); *A61B 2090/3784* (2016.02); *A61B 2576/023* (2013.01); *A61F 2/24* (2013.01); *A61N 7/00* (2013.01); *A61N 2007/0004* (2013.01); *A61N 2007/0039* (2013.01); *A61N 2007/0052* (2013.01); *A61N 2007/0086* (2013.01); *A61N 2007/0095* (2013.01)

(58) Field of Classification Search
CPC ... A61B 8/485; A61B 8/488; A61B 2576/023; A61B 2090/376; A61B 2090/3784; A61B 34/30; A61B 2090/374; A61B 2034/2063; A61B 2034/2065; A61B 2090/378; A61B 2090/3782; A61B 5/0053; A61B 8/445; A61B 8/4483; A61B 5/0215; A61N 7/02; A61N 7/00; A61N 2007/0039; A61N 2007/0052; A61N 2007/0086; A61N 2007/0095; A61N 2007/0004; A61F 2/24
USPC .......................................... 600/439, 437, 407
See application file for complete search history.

(56) References Cited

U.S. PATENT DOCUMENTS

| | | | |
|---|---|---|---|
| 5,188,106 A | | 2/1993 | Nappholz et al. |
| 5,520,188 A | | 5/1996 | Hennige et al. |
| 6,425,867 B1* | | 7/2002 | Vaezy .................. A61B 8/0833 |
| | | | 600/439 |
| 6,669,687 B1 | | 12/2003 | Saadat |
| 7,252,004 B2 | | 8/2007 | Fink et al. |
| 7,311,701 B2 | | 12/2007 | Gifford et al. |
| 7,344,509 B2 | | 3/2008 | Hynynen et al. |
| 8,938,283 B2 | | 1/2015 | Zentgraf et al. |
| 9,302,125 B2* | | 4/2016 | Gifford ..................... A61B 8/12 |
| 2002/0010392 A1* | | 1/2002 | Desai .................. A61B 5/0422 |
| | | | 600/374 |

| | | | |
|---|---|---|---|
| 2004/0147840 A1* | 7/2004 | Duggirala ................ A61B 8/00 |
| | | | 600/437 |
| 2005/0038340 A1* | 2/2005 | Vaezy ................. A61B 8/0833 |
| | | | 600/439 |
| 2005/0149008 A1* | 7/2005 | Larson ..................... A61N 7/02 |
| | | | 606/27 |
| 2005/0209588 A1* | 9/2005 | Larson ..................... A61N 7/02 |
| | | | 606/27 |
| 2006/0025683 A1* | 2/2006 | Hoffmann ............ A61B 8/0891 |
| | | | 600/439 |
| 2006/0293598 A1* | 12/2006 | Fraser ..................... A61B 8/08 |
| | | | 600/439 |
| 2007/0041961 A1* | 2/2007 | Hwang ................ A61K 38/363 |
| | | | 424/94.64 |
| 2008/0154131 A1* | 6/2008 | Lee ........................ A61B 34/20 |
| | | | 600/439 |
| 2008/0177279 A1 | 7/2008 | Sumanaweera et al. |
| 2008/0253527 A1* | 10/2008 | Boyden .................. A61B 6/145 |
| | | | 378/87 |
| 2008/0287793 A1* | 11/2008 | Hoffmann ............ A61H 31/006 |
| | | | 600/439 |
| 2008/0287803 A1* | 11/2008 | Li .......................... A61B 8/466 |
| | | | 600/466 |
| 2009/0088623 A1* | 4/2009 | Vortman .............. A61B 8/5276 |
| | | | 600/411 |
| 2009/0198093 A1* | 8/2009 | Meissner ................. A61N 7/02 |
| | | | 600/2 |
| 2010/0036253 A1 | 2/2010 | Vezina |
| 2010/0256495 A1* | 10/2010 | Kruecker ............... A61B 8/481 |
| | | | 600/458 |
| 2010/0274130 A1* | 10/2010 | Anand ..................... A61B 8/08 |
| | | | 600/439 |
| 2013/0296743 A1* | 11/2013 | Lee ........................ G16H 50/30 |
| | | | 601/3 |
| 2014/0276055 A1* | 9/2014 | Barthe .................... A61N 7/02 |
| | | | 600/439 |
| 2015/0151141 A1* | 6/2015 | Arnal ...................... A61N 7/00 |
| | | | 181/177 |
| 2018/0064412 A1* | 3/2018 | Messas ................ A61B 8/0883 |

FOREIGN PATENT DOCUMENTS

| | | |
|---|---|---|
| CN | 101888876 A | 11/2010 |
| JP | 2006-223877 A | 8/2006 |
| JP | 2008-73423 A | 4/2008 |
| JP | 2011-517284 A | 6/2011 |

OTHER PUBLICATIONS

Ryan M. Miller et al., "Histotripsy Cardiac Therapy System Integrated with Real-Time Motion Correction," Ultrasound in Medicine and Biology, vol. 39, No. 12, Dec. 1, 2013, pp. 2362-2373, XP055285001.

M. Pernot et al., "3-D real-time motion correction in high-intensity focused ultrasound therapy," Ultrasound in Medicine and Biology, 2004, vol. 30, No. 9, pp. 1239-1249.

English Translation of Notice of Rejection issued in Japanese Patent Application No. 2018-502839 dated Nov. 12, 2019.

Chinese Notification of First Office Action issued in Chinese Patent Application No. 2016800310560 dated Dec. 16, 2019.

\* cited by examiner

METHOD AND APPARATUS FOR TREATING VALVULAR DISEASE

CROSS-REFERENCE TO RELATED APPLICATIONS

This application is a National Stage of International patent application PCT/IB2016/000523, filed on Apr. 1, 2016, which claims priority to U.S. provisional application No. 62/142,096, filed on Apr. 2, 2015, the disclosures of which are incorporated by reference in their entirety.

FIELD OF THE INVENTION

The instant invention relates to methods and apparatuses for treatment or prevention of valvular diseases, in particular valvular stenosis.

BACKGROUND OF THE INVENTION

Valvular stenosis, also called heart valve disease or narrowed valve, occurs when tissues forming a cardiac valve leaflets become stiffer thereby narrowing the valve opening and reducing the amount of blood that can flow through it.

Valvular stenosis may occur in any of the four valves of the heart: the aortic valve, the mitral valve, the tricuspid valve or the pulmonic valve.

One of the known causes of valvular stenosis is a fibro-calcific degeneration of the valve leaflets wherein one or more of the valve leaflets become calcified and thus thickened and hardened, resulting in a narrowed valve opening.

Current treatments for valvular stenosis primarily involve an open or percutaneous surgery to replace the heart valve with a mechanical or tissue-based replacement heart valve.

Open surgery is done through a median sternotomy and involves a cardiopulmonary bypass of the patient. It is thus a major operation that conveys significant risk of death or serious complications. Moreover, a large class of older patients, as well as those who are frail and/or have multiple comorbidities, face significantly higher surgical risks and are thus excluded from the scope of application of this method.

Novel catheter-based approaches have been developed, such as percutaneous aortic valve replacement, which eliminate the need for open heart surgery. However, these catheter-based approaches are only applicable to selected groups of patients and still involve significant risk of death or serious complications.

Indeed it is estimated that more than 30% of the patients with severe valvular stenosis are excluded from the field of application of both open and percutaneous surgical methods.

Even when a patient fulfils the conditions to receive a replacement valve by open or percutaneous surgery, both mechanical and tissue-based replacement heart valves present significant drawbacks.

Mechanical valves are made from pyrolytic carbon and require a life-time treatment of warfarin anticoagulant, with an accompanying risk of bleeding. While such bleeding events are rare, they are often fatal.

Tissue valves (or "bioprostheses") come with no requirement for anticoagulation therapy, which reduces the incidence of bleeding. However, the lifetime of a tissue valve is typically 10 to 15 years, often less in younger patients. Over this time the valve will likely be degenerating to the point of requiring replacement, which again carries a significant risk of death. Moreover, tissue valves are also subject to valvular diseases; in particular, they may also develop fibro-calcific degeneration requiring an early replacement.

There is thus a need for a treatment or prevention of valvular stenosis that would involve a less invasive medical intervention with reduced risks, and for a treatment of valvular stenosis that would present benefits in term of long-term recovery of the patient.

The instant invention has notably for object to improve this situation.

SUMMARY OF THE INVENTION

To this aim, according to the invention, such a method for treating or preventing a valvular disease comprises:

providing an ultrasound probe located externally to a heart of a patient and able to produce ultrasound waves focused inside said heart, mapping a treatment region of a cardiac valve of the patient, said treatment region comprising at least one leaflet of the cardiac valve, controlling the ultrasound probe to emit a sequence of N focused ultrasound waves, wherein each focused ultrasound wave of the sequence of N focused ultrasound waves generates a pressure sufficient to result in cavitation at a focal spot of said focused ultrasound wave, wherein the focal spots of the sequence of N focused ultrasound waves scan the entire treatment region to soften the tissues of the treatment region.

The invention applies to the treatment of both native and tissue-based replacement valves (bioprostheses). Therefore, unless specified otherwise, the term "cardiac valve" should be construed as designating both native valves and bioprostheses.

In some embodiments, one might also use one or more of the following features:

said step of controlling the ultrasound probe to emit a sequence of N focused ultrasound waves comprises emitting the sequence of focused ultrasound waves at a predefined rate of emission, and moving the focal spot of the focused ultrasound waves to scan the entire treatment region;

said predefined rate of emission is comprised between 20 and 5000 shots per seconds;

the focal spot of the focused ultrasound waves is moved with a predefined travelling speed, said predefined travelling speed being comprised between 0.1 mm/s and 10 mm/s;

the focused ultrasound waves emitted by the ultrasound probe are (mechanically and/or electronically) steered to scan the entire treatment region;

the sequence of N focused ultrasound waves is such that a point of the treatment region is included in the focal spots of a number M of focused ultrasound waves of the sequence of focused ultrasound waves, said number M being comprised between 1 and 1000, preferably between 2 and 1000, even more preferably between 15 and 150, preferably of the order of 100;

the focal spots of the sequence of focused ultrasound waves are separated from one another by a minimal distance larger than 0.1 millimetres;

the treatment region covers a surface of at least 9 square millimetres and preferably of at least 25 square millimetres, measured in a plane perpendicular to an opening direction of the cardiac valve;

the method further comprises:

measuring an index of valvular stenosis after having controlled the ultrasound probe to emit the sequence of N focused ultrasound waves, and, until said index crosses a predefined threshold, reiterating the steps of controlling the ultrasound probe to emit a sequence of N focused ultrasound waves and measuring said index of valvular stenosis;

said index of valvular stenosis is function of a hemodynamic parameter and the step of measuring said index of valvular stenosis comprises Doppler imaging;

said index of valvular stenosis is function of a valve motion parameter and the step of measuring said index of valvular stenosis comprises estimation of valve motion;

said index of valvular stenosis is function of a shear wave propagation parameter and the step of measuring said index of valvular stenosis comprises shear wave imaging;

the method further comprises imaging the treatment region of the cardiac valve in real-time by ultrasound imaging;

the method further comprises mechanically controlling a location of the ultrasound probe externally to the heart of the patient to keep the treatment region inside a scannable region of the ultrasound probe;

a motion of the treatment region comprising at least one leaflet of the cardiac valve is estimated in real-time by ultrasound imaging and the focused ultrasound waves emitted by the ultrasound probe are steered in function of said motion of the treatment region to scan the entire treatment region;

the duration of a pressure pulse generated by each focused ultrasound wave of the sequence of focused ultrasound waves is less than 80 microseconds, preferably less than 20 microseconds, even more preferably less than 5 microseconds;

each focused ultrasound wave of the sequence of focused ultrasound waves is generated by controlling at least one transducer of the ultrasound probe to emit an emission signal in a reflective cavity of the ultrasound probe, the duration of said emission signal being less than 10 milliseconds, preferably less than 1 millisecond;

the duration of the emission signal emitted by said at least one transducer to generate said focused ultrasound wave is at least ten times longer than the duration of a pressure pulse generated by said focused ultrasound wave at a focal spot, preferably at least hundred times longer than said duration of said pressure pulse;

each focused ultrasound wave of the sequence of focused ultrasound waves generates at a focal spot a peak negative pressure half-cycle that exceeds a peak negative pressure of 5 MPa and/or a peak positive pressure half-cycle that exceeds a peak positive pressure of 10 MPa;

the treatment region further comprises at least one portion of an annulus of the cardiac valve;

said valvular disease is valvular stenosis.

Another object of the invention is an apparatus for treating or preventing a valvular disease, said apparatus comprising:

an ultrasound probe located externally to a heart of patient and able to produce ultrasound waves focused inside said heart, means for mapping a treatment region of a cardiac valve of the patient, said treatment region comprising at least one leaflet of the cardiac valve, means for controlling the ultrasound probe to emit a sequence of N focused ultrasound waves, wherein each focused ultrasound wave of the sequence of N focused ultrasound waves generates a pressure sufficient to result in cavitation at a focal spot of said focused ultrasound wave, wherein the focal spots of the sequence of N focused ultrasound waves scan the entire treatment region to soften the tissues of the treatment region.

BRIEF DESCRIPTION OF THE DRAWINGS

Other characteristics and advantages of the invention will readily appear from the following description of several of its embodiments, provided as non-limitative examples, and of the accompanying drawings.

On the drawings.

On the different Figures, the same reference signs designate like or similar elements.

DETAILED DESCRIPTION

Figure 1:
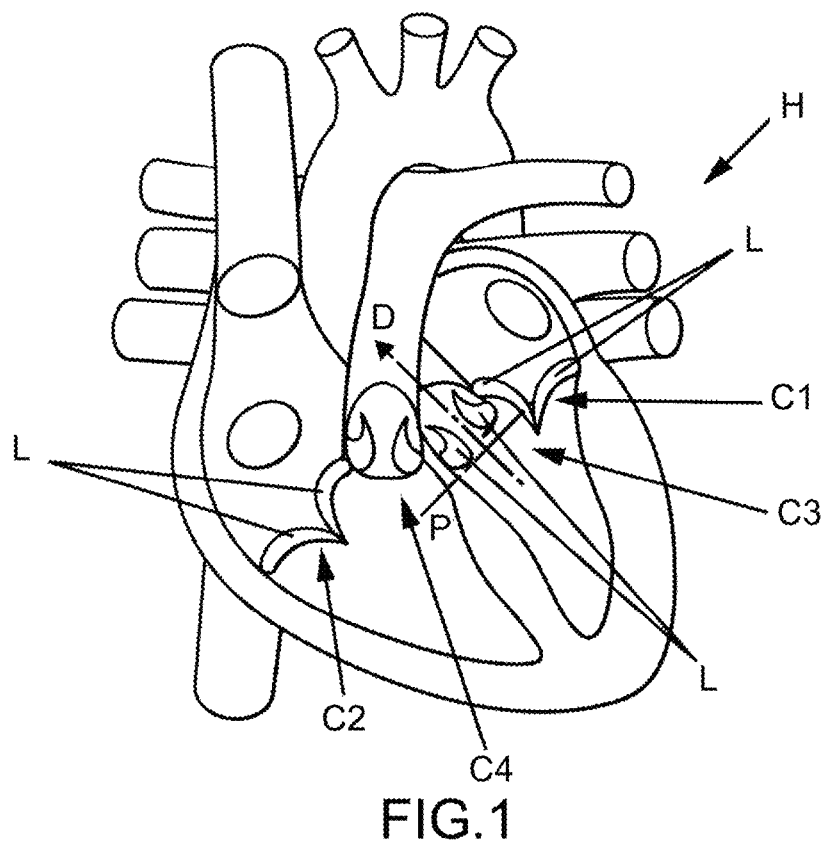
FIG. 1 illustrates a heart of a patient which is a mammalian, for instance a human.

FIG. 1 illustrates a heart H of a patient which is a mammalian, for instance a human. The heart comprises four cardiac valves C1, C2, C3, C4 that determine the pathway of blood flow through the heart: the mitral valve C1, the tricuspid valve C2, the aortic valve C3 and the pulmonary valve C4.

Each cardiac valve C allows blood to flow in only one direction through the heart H by opening or closing incumbent on differential blood pressure on each side of the valve.

More precisely, each cardiac valve C comprises leaflets L, also called cusps, which are thin tissue layers that are able to be closed together, to seal the valve and prevent backflow, and pushed (i.e. bended) open to allow blood flow. The mitral valve C1 usually has two leaflets L, whereas the three others cardiac valves C2, C3, C4 usually have three leaflets L (only two leaflets are show on FIG. 1 for each cardiac valve). The leaflets are fixed to an annulus of the cardiac valve C. The annulus is a ring composed of fibrous tissue and forming a partial or complete valvular ring around the cardiac valve C.

Valvular stenosis occurs when a cardiac valve C is narrowed. Any of the heart valves C can be affected, resulting in so-called mitral valve stenosis, tricuspid valve stenosis, pulmonary valve stenosis or aortic valve stenosis.

Valvular stenosis can arise from various causes and may be congenital (inborn) or acquired. Valvular stenosis causes serious threat to the life of the patient. In the case of aortic stenosis for instance, it is estimated that, without repair, the chance of death at five years is about 50% and at 10 years is about 90%.

In developed society, a major cause of valve stenosis is an age-related progressive calcification of the valve. It is estimated that approximately 2% of people over the age of 65, 3% of people over age 75, and 4% percent of people over age 85 are affected by this condition.

The process is currently understood as involving one or several leaflets L of a cardiac valve C becoming hardened and thickened and, as a result, the opening surface of the cardiac valve being reduced.

Cardiac valve leaflets L are thin tissue layers with a thickness normally of the order of 0.5-1.5 mm. With aging of the patient, the thickness of the leaflets L may increases to around 3-5 mm with an associated hardening of the leaflets.

A cardiac valve leaflet L is a double interface: a fluid-tissue-fluid interface. Consequently, its properties and behaviours strongly differ from bulk tissues and single tissue-fluid interfaces, such as vein walls.

Unlike a tissue-fluid interfaces that can usually be ablated or eroded without risks, the erosion of a leaflet causes high risks of perforating the leaflet thereby destroying its sealing function.

Unlike bulk tissues, a cardiac valve leaflet is a thin moving element, opening and closing at a high frequency during the cardiac cycle.

The present invention takes into account such properties and specific behaviour.

Figure 2A:
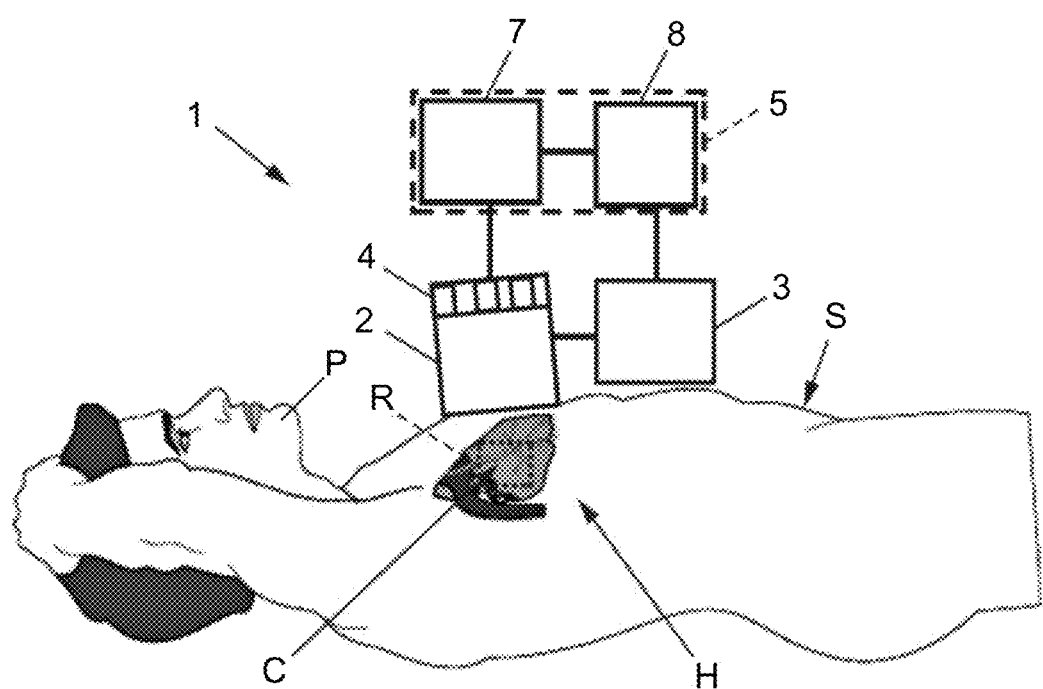
FIG. 2A illustrates an apparatus for treatment of valvular stenosis according to an embodiment of the invention.
Figure 2B:
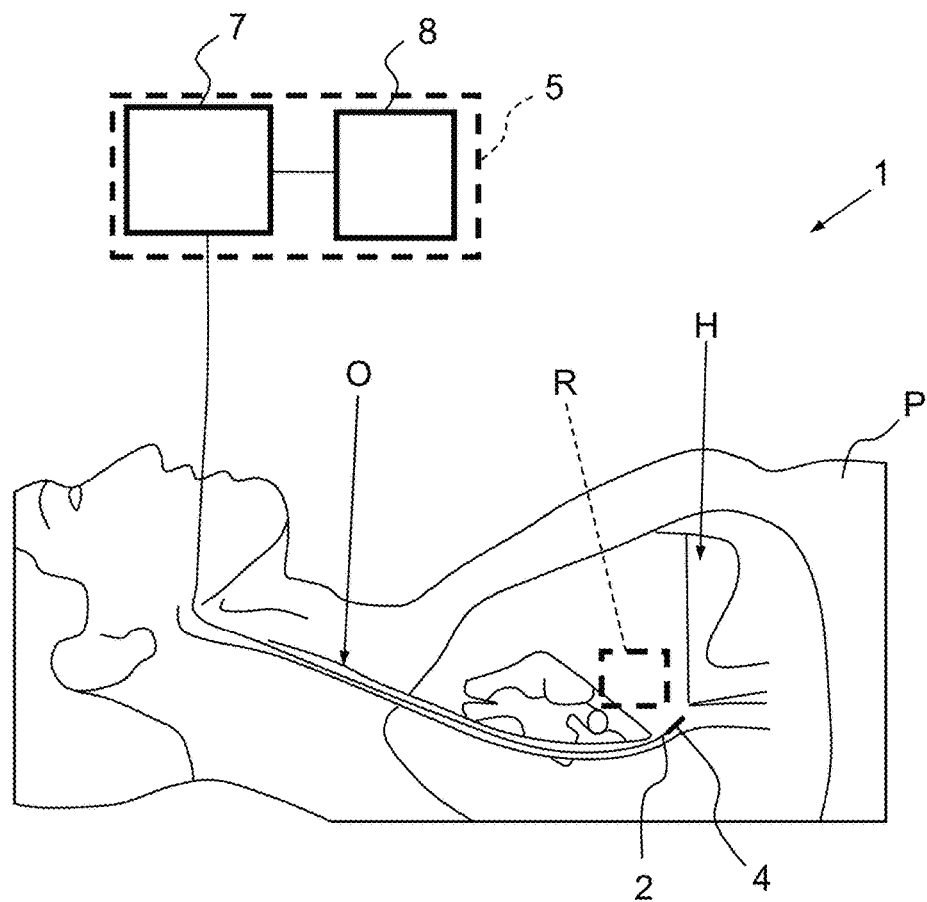
FIG. 2B illustrates an apparatus for treatment of valvular stenosis according to another embodiment of the invention.
Figure 2C:
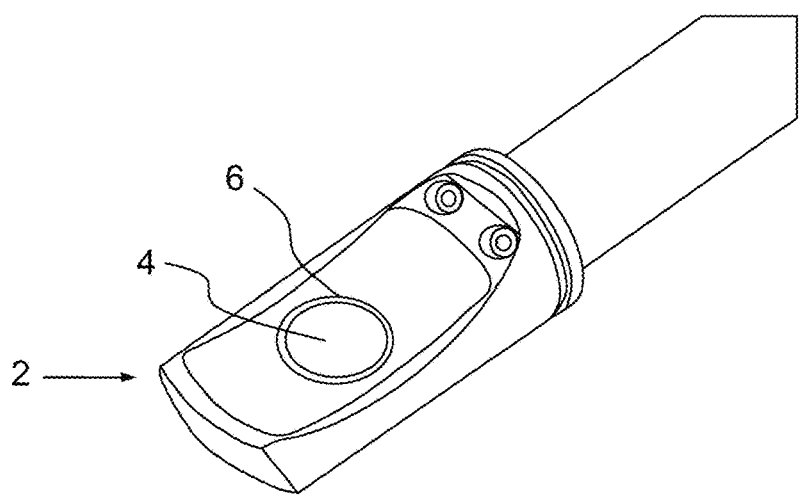
FIG. 2C is a detailed illustration of an ultrasound probe of the apparatus of FIG. 2B according to an embodiment of the invention.
Figure 3:
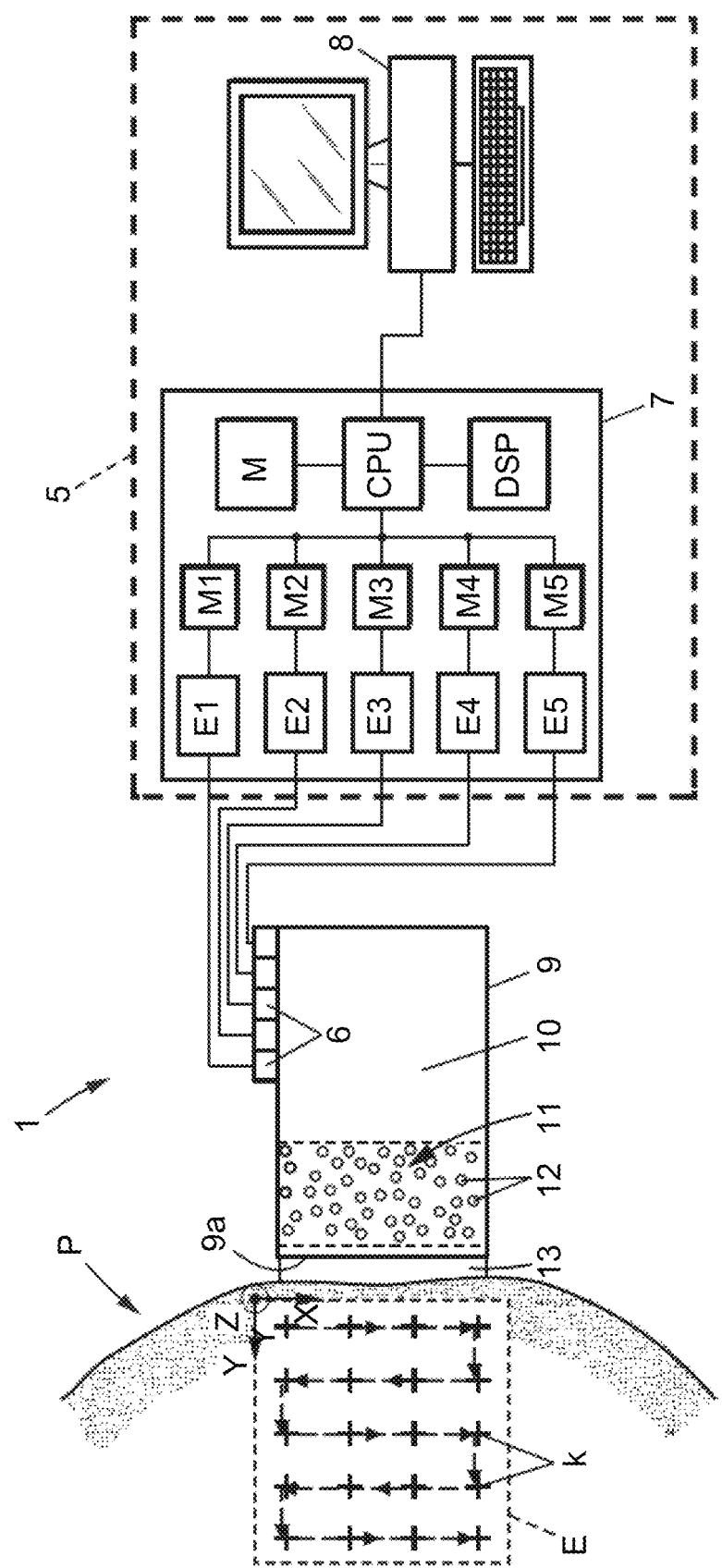
FIG. 3 illustrates a detail of the ultrasound probe of the apparatus of FIG. 2A according to one embodiment of the invention.
Figure 4:
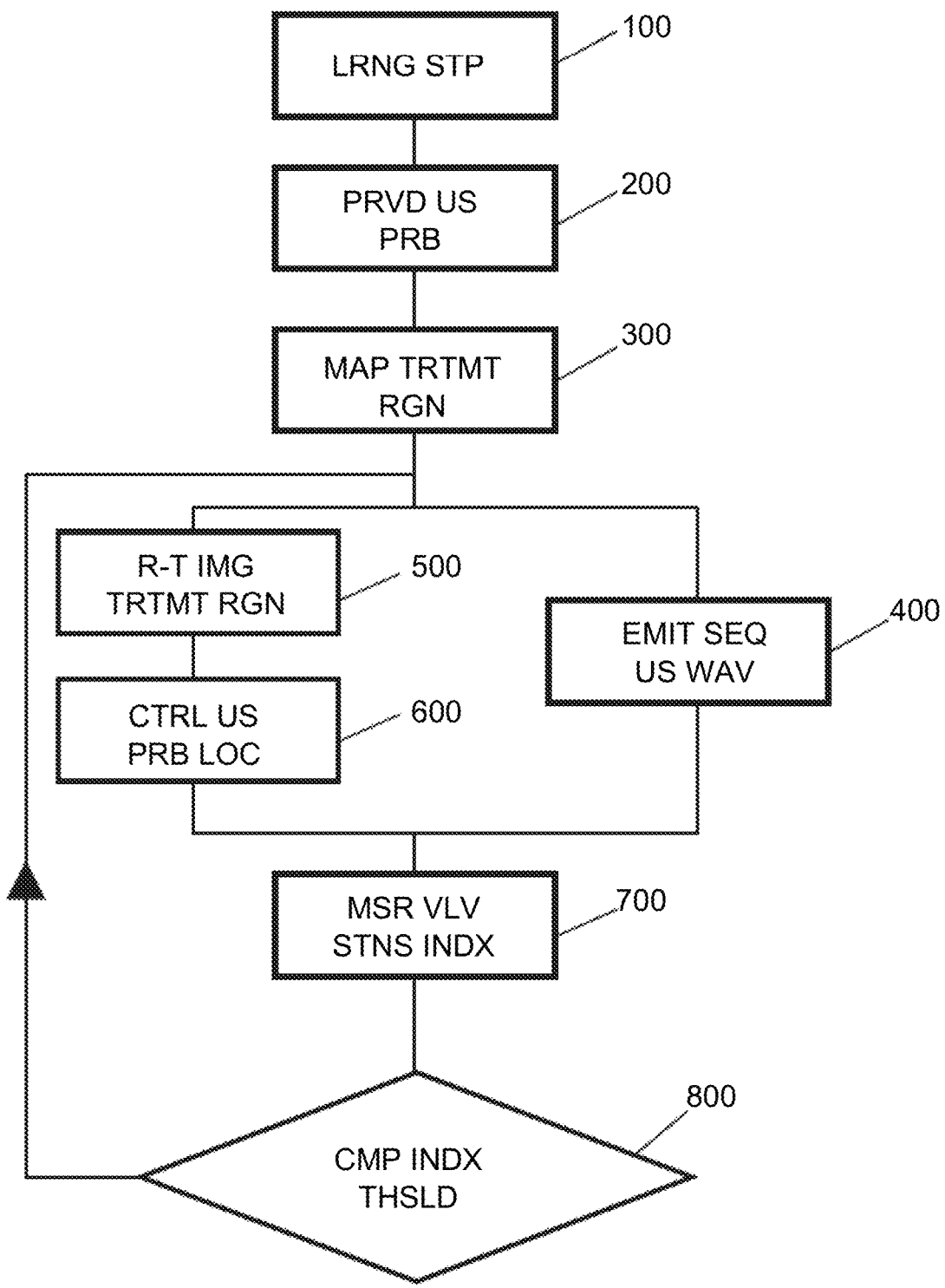
FIG. 4 is a flowchart of a method of treating valvular stenosis according to an embodiment of the invention.

We now refer also to FIGS. 2A, 2B, 2C, 3 and 4. FIGS. 2A, 2B and 2C illustrate an apparatus 1 for treatment of valvular stenosis according to several embodiments of the invention. FIG. 3 details the apparatus according to an embodiment of the invention. FIG. 4 details a method of treating valvular stenosis according to an embodiment of the invention.

The apparatus 1 comprises an ultrasound probe 2. The ultrasound probe 2 is located externally to a heart of a patient P and arranged to be able to produce ultrasound waves focused inside said patient P. The ultrasound probe 2 can be provided during a step 200 of the method illustrated on FIG. 4.

As illustrated on FIG. 3, the ultrasound probe 2 comprises at least one ultrasound transducer 6 able to produced focused ultrasounds.

The ultrasound probe 2 may further comprise a reflective cavity 9. The ultrasound transducer 6 can then be arranged to emit an emission signal inside the reflecting cavity 9 to generate a focused ultrasound wave inside the patient P.

As illustrated on FIG. 2A, the ultrasound probe 2 can be arranged externally to the patient and, for instance, in contact with the skin S of the patient P, in particular close to the heart H of the patient P. This way, the method according to the invention may be non-invasive.

In another embodiment, illustrated on FIG. 2B and FIG. 2C, the ultrasound probe 2 may be introduced inside the oesophagus O of the patient P and brought in proximity with the heart H of the patient P.

In yet another embodiment, not illustrated on the drawings, the skin and/or bones of the patient may be pushed aside during a preliminary surgical operation so that the ultrasound probe 2 can be arranged in closer proximity to the heart H. In a variant, the ultrasound probe 2 may also be introduced under the skin and/or bones of the patient to be arranged in close proximity to the heart H. For instance a sternotomy may be performed and the ultrasound probe 2 may be brought in contact with the external wall of the heart of the patient.

The apparatus 1 also comprises means 4—e.g. an imaging device, and more particularly an ultrasonography (echography) probe—for mapping a treatment region R of a cardiac valve V of the patient P, the treatment region R comprising at least one leaflet L of the cardiac valve V.

Said at least one leaflet L of the cardiac valve V may be calcified leaflet(s), in particular in the case of a method for treatment of valvular disease.

The at least one leaflet L may also be stiff leaflet(s), for instance in the case of a method for preventing valvular disease.

The treatment region R may also comprises at least one portion of an annulus of the cardiac valve, in particular a stiff or calcified portion of the annulus.

In one embodiment of the invention, the means for mapping 4 can be an ultrasound imaging array, and can, in particular, be the array of transducer 6 of the ultrasound probe 2 used for generating focused ultrasound waves, as illustrated on FIG. 2A.

In a variant, the means for mapping 4 may comprise an ultrasound imaging array 4 integrated in the ultrasound probe 2 and separated from the array of transducer 6 used for generating focused ultrasound waves.

One example of such an embodiment is illustrated in detail on FIG. 2C where a central element 4 of the catheter ultrasound probe 2 comprises the ultrasound imaging array 4 of the means for mapping 4 and a surrounding element 6 comprises the array of transducer 6 used for generating focused ultrasound waves.

On the example of FIG. 2C, the central element 4 has the shape of a disc but it may also present the shape of a rectangle or another suitable shape. Moreover, the surrounding element 6 is shown with the shape of a circular annulus but may adopt other suitable shapes such as a rectangle ring or dots for instance.

The surrounding element 6 may be divided in several elements, for instance several concentric rings 6 that can be independently controlled.

The ultrasound imaging array 4 may acquire images in various imaging modes such as A-mode, B-mode, CW-Doppler, PW-Doppler, Color Doppler, Power Doppler, M-mode, Harmonic Imaging, Shear wave imaging, Elasticity Imaging, Tissue Strain Imaging, this list being not limitative.

In other embodiments of the invention, the means for mapping 4 may comprises a CT scanning apparatus, an X-ray imaging apparatus or an MRI apparatus for instance.

By "mapping", it is meant that a digital image of the treatment region R is obtained during a mapping step 200. The digital image may for instance be stored in a memory. The digital image of the treatment region R may thus be obtained by ultrasound imaging, CT scanning, X-ray imaging or MRI, for instance.

The treatment region R can cover a surface of at least 25 square millimetres, measured in a plane P perpendicular to an opening direction D of the cardiac valve V.

By "opening direction", it is meant a general direction D of the blood flowing through the cardiac valve V when said valve is open as illustrated on FIG. 1.

As illustrated on FIG. 1, the apparatus 1 also comprises a controller 5 of the ultrasound probe 2.

We now refers also to FIG. 3 which illustrates a detail of the ultrasound probe 2 of FIG. 2, according to an embodiment the invention.

The ultrasound transducers array 6 can comprise a few tens to a few hundred transducers 6. The array 6 may be a linear array, with the transducers arranged side by side along a longitudinal axis of the array. The array 6 can also be a two-dimensional array so as to emit three-dimensional focused waves.

The controller 5 of the ultrasound probe 2 may then comprises for instance:

an electronic system 7 able to command the transducer array 6 to fire ultrasound waves and, if needed, to acquire ultrasound signals; and a microcomputer 8 for controlling the electronic system 7.

As shown on FIG. 3, the electronic system 7 may include for instance:

n digital/analog converters ($E_1$-$E_n$) individually connected to the n transducers ($T_1$-$T_n$) of the transducer array 6;

n buffer memories ($M_1$-$M_n$) respectively connected to the n digital/analog converters, a central processing unit (CPU) communicating with the buffer memories and the microcomputer 8, a memory (M) connected to the central processing unit;

a digital signal processor (DSP) connected to the central processing unit.

The transducers T1-Tn are controlled independently of one another by the central processing unit.

In a step 400 of the method according to the invention, the controller 5 controls the ultrasound probe 2 to emit a sequence of N focused ultrasound waves.

The ultrasound probe 2 emits focused ultrasound waves that generate negative pressure inside the tissues of the heart H of the patient P.

More precisely, the ultrasound probe 2 is controlled so that each focused ultrasound wave of the sequence of N focused ultrasound waves generates, at the focal spot, a pressure pulse sufficient to result in cavitation. A focal spot may be defined precisely as the volume wherein the ultrasound pressure exceeds the cavitation threshold.

The resulting cavitation may form a bubble cloud at a focal spot of the focused ultrasound wave. Such acoustic cavitation occurs when the acoustic intensity or pressure exceeds a threshold of the tissue (cavitation threshold).

To this aim, the ultrasound probe 2 may for instance emit focused ultrasound waves that generate, at their focal spot, a peak negative pressure half-cycle that exceeds a peak negative pressure of 5 MPa, for instance present an absolute value higher than 10 MPa.

At their focal spot, the peak positive pressure half-cycle of the focused ultrasound waves may also exceeds a peak positive pressure of 10 MPa, for instance present an absolute value higher than 50 MPa.

The duration of the pressure pulse generated by each focused ultrasound wave at the focal spot may be less than 80 microseconds, or even 20 microseconds.

In one example, the duration of each focused ultrasound wave is less than 5 microseconds.

This way, the sequence of N focused ultrasound waves does not heat the tissues of the heart which prevent damaging the heart valve and the surrounding structures of the heart.

The method and apparatus of the invention thus prevent erosion and heating of the tissues of the heart and preserve structures surrounding the cardiac valves.

The sequence of focused ultrasound waves is also such that the focal spots k of the sequence of N focused ultrasound waves scan the entire treatment region R.

By "scan the entire treatment region", it is meant that the centres of the focal spots k of the sequence of N focused ultrasound waves are arranged to fill the entire treatment region R with a given minimal distance separating the centre of each focal spots k and a given maximal distance separating the centre of each focal spots k from its nearest neighbour.

The centre of each focal spots may be separated from its nearest neighbour by a given maximal distance of less than 1 millimetre.

In one embodiment, the centre of each focal spots of the sequence of focused ultrasound waves may be separated from one another by a minimal distance larger than 0.1 microns, for instance larger than 0.1 millimeter.

In a variant, some focused ultrasound waves of the sequence of focused ultrasound waves may present focal spots that have the same location inside the treatment region R.

The focused ultrasound waves of the sequence of focused ultrasound waves may be periodically spaced or may be grouped on some predefined locations of the treatment region R.

FIG. 3 illustrates on example of the centres of the focal spots k of a sequence of N focused ultrasound waves. The order of emission of the sequence of N focused ultrasound waves is illustrated by dashed arrows connecting the centres of focal spots k as matter of non-limitative example.

According to some embodiments of the invention, neighbouring focal spots may overlap; otherwise stated, the maximal distance between their centres may be smaller than their width. This ensures that all the points of the treatment region R (or of at least a connected subset thereof) are exposed at least once to ultrasound waves whose intensity is sufficient to induce cavitation.

According to alternative embodiments of the invention, neighbouring focal spots may not overlap, their centres being separated by distances larger than their widths. In this case, only discrete locations of the treatment region R are exposed at least once to ultrasound waves whose intensity is sufficient to induce cavitation.

An hybrid approach may also be followed, wherein some neighbouring focal spots overlap, while other do not.

By using such a sequence of N focused ultrasound waves, it is possible to soften the tissues of the calcified cardiac valve leaflet L while preventing erosion of said tissues, and thus a puncture of the cardiac valve leaflet L.

It is thus possible to restore leaflet mobility and valve function in patient.

An ultrasound probe 2 suited for emitting such high intensity controlled focused ultrasound waves is illustrated on FIG. 3.

In the illustrated embodiment, the ultrasound probe 2 comprises a reflective cavity 9 and at least one transducer 6.

The reflective cavity 9 may be filled with a liquid 10, for example water and in which the ultrasound transducers array 6 are located. The reflective cavity 9 comprises walls made of a material forming a highly reflective interface for acoustic waves, for example thin films separating the liquid contained in the cavity from the air outside the cavity.

The reflective cavity 9 may be in contact at one of its ends with the patient P through a window 9a in the cavity wall, directly or through an acoustic lens 13 mounted on the window 9a.

The reflective cavity 9 may further comprises a multi-scattering medium 11 adapted to be traversed by acoustic waves emitted by the ultrasound transducers before said waves reaches the patient's body. The multi-scattering medium 11 is able to cause multiple scattering of said acoustic waves.

The multi-scattering medium 11 is located, for example, near the window 9a of the reflective cavity 9 and comprises a number of scatterers 12, for instance between several tens to several thousands of scatterers 12.

The scatterers 12 are adapted to scatter acoustic waves and are advantageously distributed randomly or non-periodically in the multi-scattering medium 11, meaning that their distribution does not exhibit a periodic structure. The scatterers 8a may thus exhibit a surface having a significant difference in impedance compared to the medium of the reflective cavity.

The scatterers 12 can have the general shape of vertical rods held in place by frames or attached to the walls of the reflective cavity. Alternatively, the scatterers 12 may take the form of beads, granules or cylinders and be held in place by foam, an elastomer, or three-dimensional frames so that they are distributed over all three dimensions of the space to form the multi-scattering medium 11.

The scatterers 12 may, for example, have transverse cross-sections that are substantially between 0.1 and 5 times the wavelength of the wave in the reflective cavity, for example between 0.5 and 1 times said wavelength. Said transverse cross-section is understood to be a cross-section taken perpendicularly to the extension direction of the scatterers 12 and/or to the longest extension direction of the multi-scattering medium 11.

The scatterers 12 can be distributed within the multi-scattering medium 11 so that their surface density in a cross-section of the multi-scattering medium 11 transverse to the extension direction Z of the scatterers 12, is, for an acoustic wave having a centre frequency of about 1 MHz, ten or so scatterers 12 per square centimetre, for example eighteen acoustic scatterers 12 per square centimetre.

In the case of a three-dimensional multi-scattering medium, the scatterers 12 can be distributed in the multi-scattering medium 11 so that their volume packing density within the multi-scattering medium 11 is between 1% and 30%.

The length of the multi-scattering medium 11, along the direction of propagation of the wave, may be a few centimetres, for example two centimetres.

The array 6 of ultrasound transducers can be arranged on a face of the reflective cavity 9 facing the window open on the patient's body or may be oriented so as to emit waves toward the multi-scattering medium 11, at a certain angle relative to a cavity extension direction Y, for example 60°.

Such a reflective cavity 9 forms a reverberator that permits, at the same time, to finely control the location of the focal spot of ultrasound waves emitted by the ultrasound probe 2, and to amplify the pressure of an acoustic wave generated by the ultrasound transducer array 6 by more than 20 dB.

To this aim, prior to performing the method of treatment according to the invention, a calibration 100, or learning step 100, of the ultrasound probe 2 may be conducted.

Such a calibration may involve the determination of matrix of individual emission signals eik(t) such that, to generate a focused ultrasound wave s(t) focused at a target point k of the treatment region R, each transducer i of the array 6 emits an emission signal:

$$S_i(t) = e_{ik}(t) \otimes s(t).$$

These individual emission signals are ultrasound signals that may be determined by calculation (for example using a spatio-temporal inverse filter method), or may be determined experimentally during a preliminary learning step 100.

During an example of such a learning step 100, an ultrasonic pulse signal may be emitted by a hydrophone, successively placed at a succession of target points k in a volume of liquid placed in contact with the ultrasound probe 2. The signals $r_{ik}(t)$ received by each transducer i of the array 6 from the emission of said ultrasonic pulse signal are captured. The signals $r_{ik}(t)$ are then converted by the analog-to-digital converters and stored in the memory connected to the processor CPU, which then calculates the individual emission signals $e_{ik}(t)$ by time reversal of said received signals:

$$e_{ik}(t) = r_{ik}(-t).$$

When one or more focused ultrasound waves are then to be focused on a predetermined target point k within the treatment region R, the ultrasound probe 2 is placed in contact with the patient P, and an emission signal $S_i(t)$ is emitted by each transducer i of the array 6 to generate a focused ultrasound wave:

$$S_i(t) = e_{ik}(t) \otimes s(t).$$

The duration of the emission signal emitted by each transducer of the array 6 to generate a focused ultrasound wave of the sequence of focused ultrasound waves may be less than 10 milliseconds, in particular less than 1 millisecond.

The duration of the pressure pulse generated by said focused ultrasound wave at the focal spot may be at least 10 times shorter, and preferably at least one hundred times shorter, than the duration of the emission signal emitted by each transducer of the array 6. Otherwise stated, the duration of the emission signal emitted by each transducer of the array 6 to generate a focused ultrasound wave of the sequence of focused ultrasound waves may be at least ten times longer than the duration of the pressure pulse generated by said focused ultrasound wave at the focal spot, preferably at least hundred times longer than the duration of said pressure pulse.

Therefore, the duration of the pressure pulse may be of less than 1 millisecond, preferably of less than 100 microseconds, even more preferably of less than 100 microsecond; for example, the emission signal may has a duration of the order of 800 microseconds and the pressure pulse at the focal point a duration of less than 5 microseconds.

Different ultrasound probes may also be used to carry out the inventive method. FIGS. 5A to 5D illustrate different exemplary embodiments of such probes.

Figure 5A:
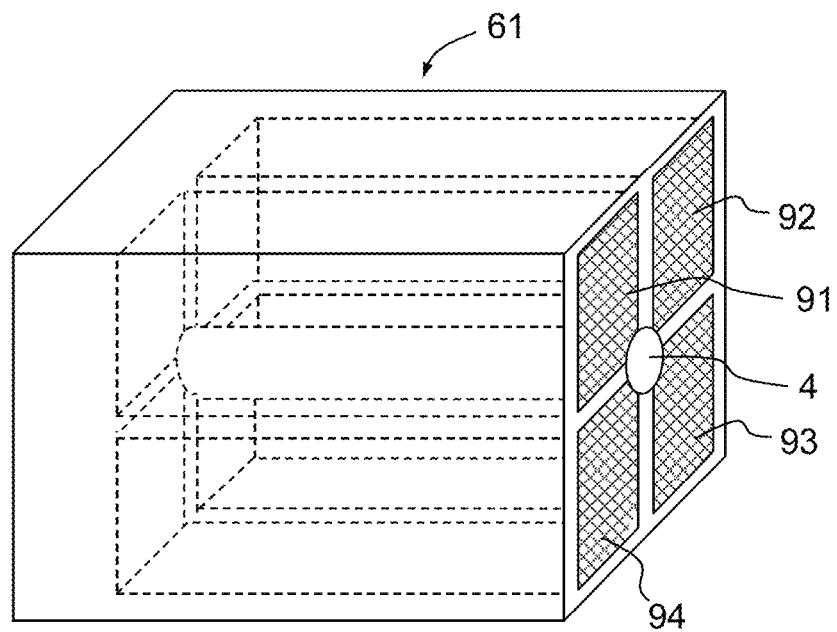
FIGS. 5A to 5D are schematic illustrations of different ultrasound probes according to respective embodiments of the inventions.

The ultrasound probe 61 of FIG. 5A comprises an assembly of four reflective cavities 91, 92, 93, 94, each one similar to that of FIG. 3, forming a square. An imaging array 4 is situated at the centre of the assembly. The reflective cavities are coupled to the patient's body through respective plastic bags filled with gel (not represented) while the imaging array 40 is almost directly in contact with it (in practice, with the interposition of a plastic sheet interconnecting the bags and of a thin layer of gel).

Figure 5B:
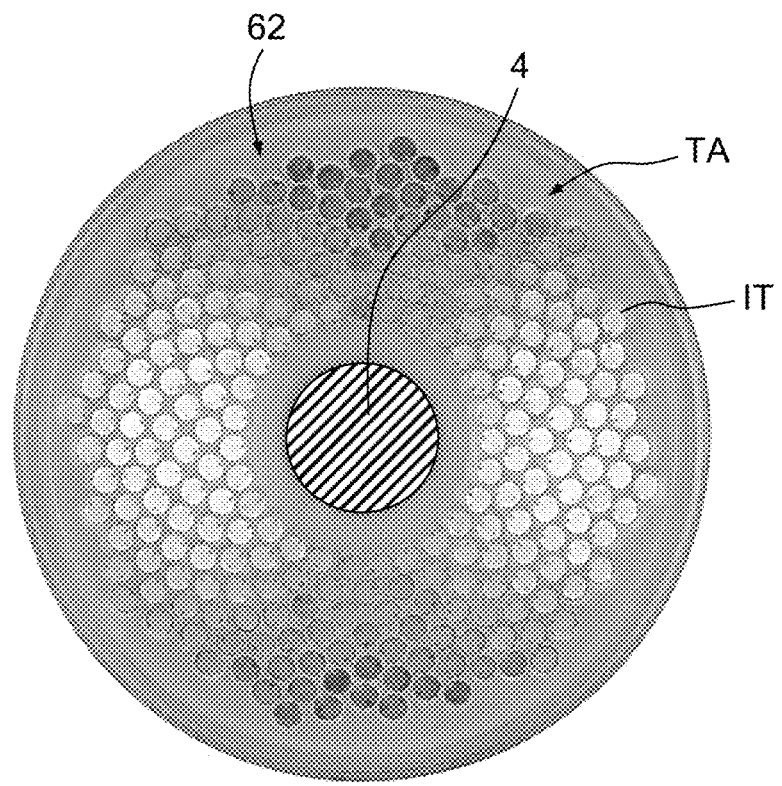

The ultrasound probe of FIG. 5B comprises a multi-element transducer 62 consisting of a bi-dimensional array TA of several tens or hundreds of independently-driven elementary transducers (one of which is designated by reference IT). An imaging array 4 may be situated at the centre of the multi-element transducer, in order to be in direct—or almost direct—contact with the patient's body. This embodiment allows electronically steering the focused ultrasound waves, like the embodiments based on reflective cavities; its main drawback is the complexity of the controller 5, which has to comprise several tens or hundreds of independent power drivers for the individual elementary transducers.

Figure 5C:
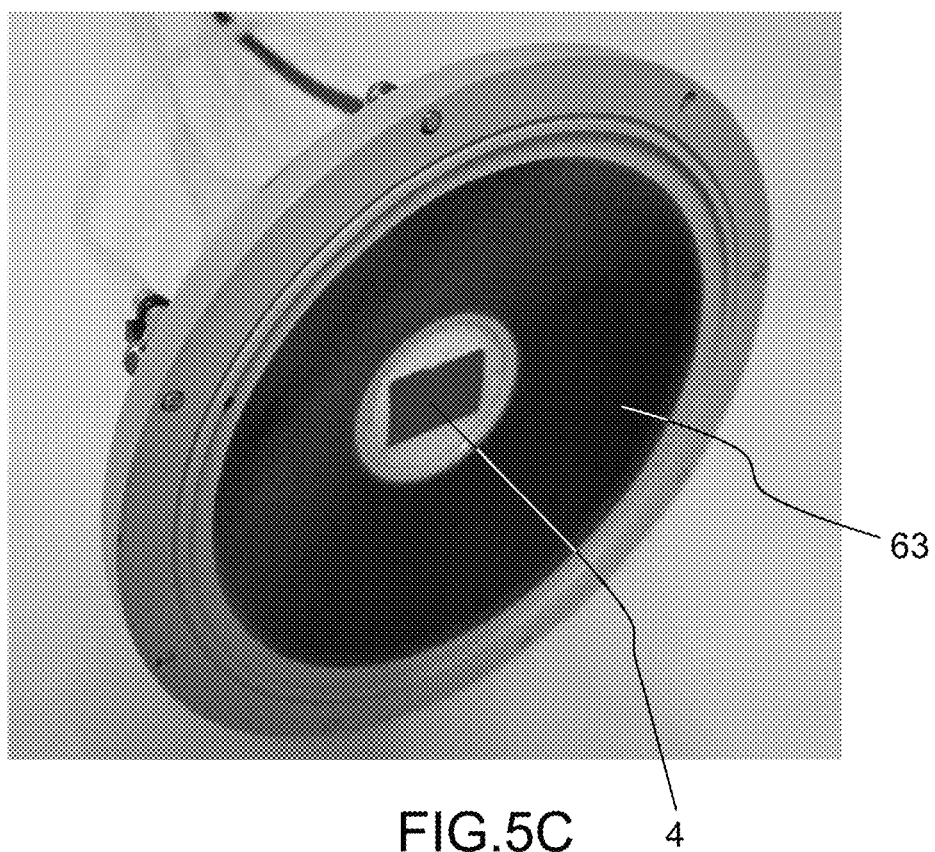

FIG. 5C shows a much simpler ultrasound probe, based on a concave mono-element transducer 63, focusing ultrasound waves at a fixed depth. An imaging probe 4 is situated at the centre of the mono-element transducer. In this case, the focused ultrasound waves have to be mechanically steered, e.g. by displacing the transducer along three axes. A significant drawback is that, in order to allow a displacement of the transducer in the axial direction, the imaging array cannot be kept in direct contact with the body of the patient; imaging has then to be performed through a significant depth of matching gel, which reduces the quality of the acquired images.

Figure 5D:
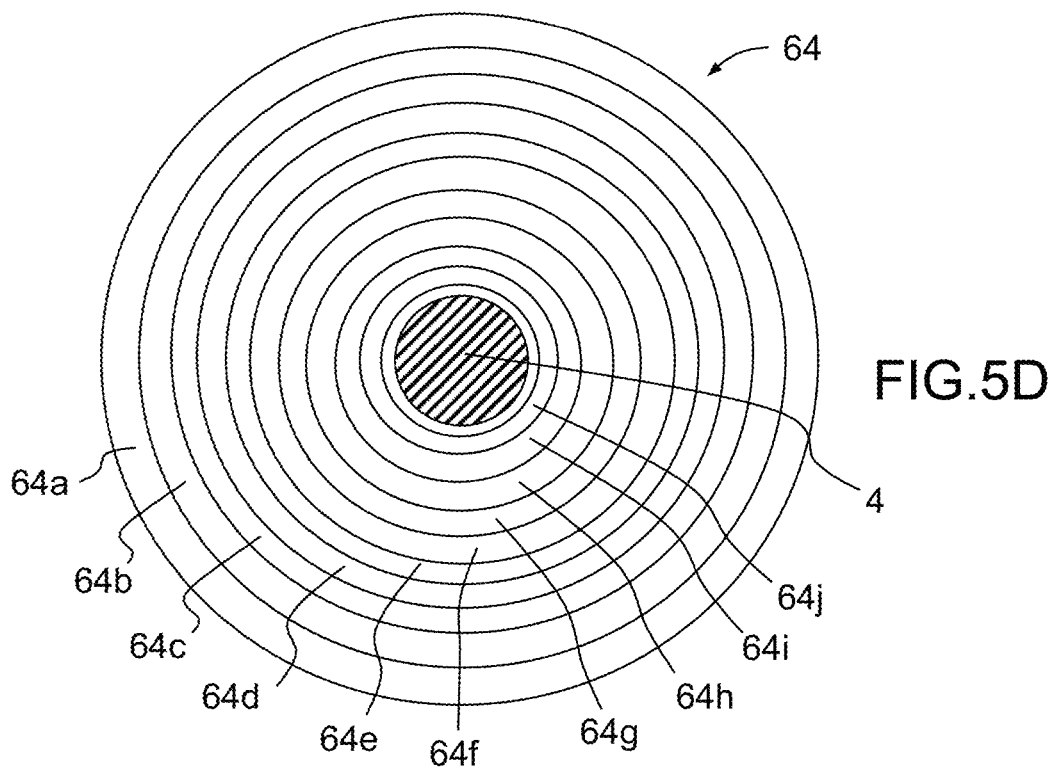

FIG. 5D illustrates an annular array transducer 64, consisting of a limited number (typically 5 to 20, 10 in the example of the figures) of concentric ultrasound annular transducers 64a-64j. Driving the annular transducers with an appropriate phase difference allows focusing an ultrasound wave at an adjustable depth. In-plane scanning is performed mechanically, by moving the transducer. Imaging probe 4 is situated at the centre of the innermost annular element. The complexity of the driver 5 is much lesser than in the case of FIG. 5B, due to the reduced number of power drivers; moreover, unlike the case of FIG. 5C, the imaging probe may be kept in contact with the patient's body, as the scanning in the axial direction is performed electronically. Document U.S. Pat. No. 5,520,188 discloses an annular array transducer of this kind.

An ultrasound probe suitable for the invention may be optimized to focus ultrasound energy in a predefined region, called a scannable region E illustrated on FIG. 3.

A scannable region E is a region of the patient body where the focusing of ultrasound energy by the ultrasound probe is more efficient and/or is calibrated.

The scannable region E may be predefined during the preliminary learning step mentioned. The scannable region can for instance be defined by the succession of target points k where the hydrophone has been successively located during the preliminary learning step.

The method according to the invention may also comprise a real-time imaging 500 of the cardiac valve, to map the treatment region. In this embodiment, the step of real-time imaging of the cardiac valve may further allow to map the scannable region of the ultrasound probe.

A mechanical control 600 of the location of the ultrasound probe externally to the heart of the patient may then be used to keep the treatment region inside the scannable region of the ultrasound probe.

To this aim, the ultrasound probe 2 can be mounted on a robotic arm 3, or holder, able to control the location of the ultrasound probe 2 with regard to the patient's heart H location. The robotic arm 3, driven by controller 5, may control the location of the ultrasound probe to keep the treatment region inside the scannable region of the ultrasound probe.

We will now describe in greater details how a controlled softening of the tissues of a cardiac valve leaflet L can be obtained by selecting the timing, duration and focal spot location of each focused ultrasound waves.

In one embodiment of the method of treatment according to the invention illustrated on FIG. 4, the sequence of focused ultrasound waves is thus emitted at a predefined rate of emission while the focal spot of the focused ultrasound waves is moved to scan the entire treatment region R.

The predefined rate of emission may be for instance comprised between 20 and 5000 shots per seconds, preferably between 50 and 1000 shots per seconds. In one example, the rate of emission may be about 100 shots per second. In another example it may be about 250 shots per second.

The focal spot of the focused ultrasound waves may be moved to scan the entire treatment region with a predefined travelling speed. The predefined travelling speed may be comprised between 0.1 mm/s and 10 mm/s, preferably of the order of 1 mm/s.

In one embodiment of the invention, the focused ultrasound waves emitted by the ultrasound probe 2 can be steered to scan the entire treatment region R.

For instance, the ultrasound probe 2 illustrated on FIG. 3, and described here before, may be able to electronically steer the focused ultrasound waves to scan the entire treatment region R.

By "the focused ultrasound waves are electronically steered", it is meant that the successive locations of the focal spots of the focused ultrasound waves are selected without physically moving the ultrasound probe 2, it this meant that the focal spot of focused ultrasound waves emitted by the ultrasound probe 2 can be moved without physically moving the ultrasound probe 2 but by controlling the emission signals of the transducers 6 of the ultrasound probe 2.

Alternatively or in addition, the location of the ultrasound probe 2 may be mechanically controlled 600, e.g. using the robotic arm 3 or different mechanical actuators, in function of said motion of the treatment region, in order to scan the entire treatment region.

Real-time imaging 500 may also be used to estimate a motion of the treatment region R with regard to the ultrasound probe 2; in the case of a heart valve, motion of the treatment region results mainly from a combination of breathing and hearth beat. The focused ultrasound waves emitted by the ultrasound probe 2 may then be steered in function of said motion of the treatment region, in order to scan the entire treatment region. Otherwise stated, real-time imaging 500 may allow performing real-time tracking of the valve to be treated. A tracking algorithm suitable to be used in the invention is discussed in the paper by R. M. Miller et al. "Histotripsy cardiac therapy system integrated with real-time motion correction", Ultrasound in Med. & Biol. Vol. 39, No. 12 pp. 2362-2373, 2013. Another suitable tracking algorithm is described in M. Pernot et al. "3-D real-time motion correction in high-intensity focused ultrasound therapy" Ultrasound in Med Biol 2004, 30, 9, 1239-1249.

This way, motions of the treatment region R can be compensated for by electronical steering of the focused ultrasound waves and/or mechanical control of the location of the ultrasound probe 2.

More precisely, the focused ultrasound wave emission may be driven by the following process, carried out by the controller 5:

1. The imaging array 4 is adjusted to the ultrasound transducers array 6 in order to provide images of the treatment region (a cardiac valve or a portion thereof) in real time.

2. The imaging array 4 and the ultrasound transducers array 6 are calibrated together in order to locate the focused ultrasound waves emission into the viewable treatment region provided by the imaging array 3. Thanks to the images flow provided by the imaging array, an image processing algorithm tracks the cardiac valve in real time:

3.1 The first step of the algorithm is user dependent and consists in segmenting the position of the cardiac valve in a given fixed images, showing the cardiac valve in its closed state. The result of this first step will be called the initial valve segmentation.

3.2 The second step of the algorithm is automatic and consists in retrieving and tracking the cardiac valve into the real time ultrasound images flow using the initial valve segmentation. This step is based on the state of the art algorithm in matter of object tracking such as region-based, contour-based, template-based methods; see e.g. the above-referenced paper by M. Pernot et al (2004) and R. M. Miller et al (2013).

3.3. The third step of the algorithm consists in providing accurate information about the position of the focal spot onto or outside the cardiac valve in real time. This information will be given in percentage of confidence. If the percentage of confidence is too low, for security reasons the ultrasound wave emission will be stopped. Otherwise, the ultrasound wave emission is authorized, and if necessary the ultrasound probe 6 is steered—electronically and/or mechanically—in order to adjust the position of the focal spot onto the valve.

Typically, the controller 5 will be configured to perform the electronical and/or mechanical steering of the focused ultrasound waves in order to scan the target reason to be treated while tracking its motion during the treatment. On the contrary, in the above-referenced paper by R. M. Miller et al., tracking is used to keep ultrasound pulses focused on a same point of a heart.

It is possible to predefine a plurality of N successive insonification times $t_1$-$t_N$ and/or a plurality of N cavitation locations $P_1$-$P_N$ inside the treatment region.

In one variant, the successive insonification times and the cavitation locations may be computed to correspond to a travelling speed of the focal sport comprised between 0.1 mm/s and 10 mm/s, preferably of the order of 1 mm/s.

Alternatively, the successive insonification times and the cavitation locations may be computed to correspond to alternate trajectory of the focal spot that may then correspond to a travelling speed of the focal sport higher than 10 mm/s.

As already mentioned above, the centre of each focal spots of the sequence of N focused ultrasound waves may be separated from one another by a minimal distance shorter than a diameter (more generally, a width) of the focused ultrasound waves focal spots.

This way, a point of the treatment region may be included in the focal spots of several focused ultrasound waves, and each point of the treatment region is included in the focal spot of at least one focused ultrasound wave. As a matter of non-limitative example, the diameter of the focal spots of the focused ultrasound waves may be about 1 mm.

The sequence of N focused ultrasound waves may be such that a point of the treatment region is included in the focal spots of a number M of focused ultrasound waves of the sequence of focused ultrasound waves, said number M being comprised between 1 and 1000, preferably between 2 and 1000, preferably of the order of 100.

Alternatively, the centres of at least some focal spots of the sequence of N focused ultrasound waves may be separated from one another by a minimal distance longer than a diameter (more generally, a width) of the focused ultrasound waves focal spots. This way, at least some points of the treatment region may not be included in the focal spots of any focused ultrasound wave. In some cases, the centre of each focal spots of the sequence of N focused ultrasound waves may be separated from one another by a minimal distance longer than a diameter (more generally, a width) of the focused ultrasound waves focal spots.

As illustrated on FIG. 4, the method according to the invention may also comprise a step of using a measuring device (which, in some embodiment, may be or include the imaging array 4 itself) for measuring an index of valvular stenosis 700 after having emitted the sequence of focused ultrasound waves.

In one embodiment of the invention, the index of valvular stenosis is a function of a hemodynamic parameter. The hemodynamic parameter may for instance be a heart pressure gradient across the cardiac heart valve or a blood flow velocity across the cardiac heart valve. These parameters may be measured using e.g. a Swan-Ganz catheter of a Millar catheter. However, use of such catheters is not preferred because it is invasive.

In another embodiment, performed hemodynamic parameter may be determined by using Doppler imaging to measure the blood flow velocity across the cardiac heart valve. Doppler imaging may be performed by a Doppler imager, which may include the imaging array 4, or a dedicated imaging device.

In another embodiment that may be combined with the previous embodiment, the index of valvular stenosis can be function of a shear wave propagation parameter. In this embodiment, the step of measuring the index of valvular stenosis may thus comprise a shear wave imaging step carried out using a shear wave imaging device, as described in document U.S. Pat. No. 7,252,004 for instance.

In yet another embodiment that may be combined with one or both of the previous embodiments, the index of valvular stenosis may be function of a valve motion parameter. The step of measuring said index of valvular stenosis may then comprise an estimation of a valve motion, e.g. obtained by Doppler imaging.

In both embodiments, the index of valvular stenosis may then be compared 800 with a predefined threshold. This way, it is possible to assess the progress of the method according to the invention. The predefined threshold may be representative of tissues softness to be achieved.

In one embodiment of the invention, at least the steps of controlling 400 the ultrasound probe to emit a sequence of N focused ultrasound waves and measuring 700 the index of valvular stenosis may then reiterated until the index of valvular stenosis reaches, or crosses, the predefined threshold.

Several series of N focused ultrasound waves may thus be emitted, separated by steps of control to assess the state of the cardiac heart valve tissues and its evolution.

The inventive method has been tested experimentally.

To this aim, Carpentier-Edwards Perimount Magna™ aortic valve bioprostheses, explanted on humans, were used as model of heart calcified valve. The indication of explant was a significant stenosis with calcification. Each valve was fixed in glutaraldehyde 0.6% immediately after explant.

Before each experimentation, the valve was immersed in saline serum (0.9% NaCl) during 5 minutes, three consecutive times.

The protocol was in agreement with institutional guidelines (French national reference number of the study: 02255.02).

A 1.25 MHz focused single-element transducer (Imasonic®, Besancon, France), called hereafter a "therapy transducer", was used to generate focused ultrasound waves. It had a 100 mm focal length (f-number=1). This transducer was driven by a high-voltage amplifier. The therapy transducer was used to generate 10-cycle pulses, each 8 μs long, delivered at a pulse repetition frequency (PRF) of 100 Hz. It is estimated the pressure peak amplitudes at the focal spot was 70 MPa and −19 MPa respectively for the positive and negative peak.

3D Echocardiography was used to guide and monitor the treatment. An IE33 (Philips™) scanner and X5-1 probe (xMATRIX™ array, 3 MHz, 3040 elements with micro-beam-forming) were used. The imaging probe was fixed through a hole in the center of the therapy transducer. The focal spot of the therapy transducer was positioned on the central axis of the imaging probe at a depth of 100 mm. A bi-plane imaging mode with two imaging planes set at 90° was used during the whole procedure. The histotripsy focal spot was visible within the two imaging planes. The combination of therapy transducer and imaging probe was called the "therapy device". The same material was used for in vitro and in vivo procedures.

For all the procedures, sequences of 10 minutes of ultrasound waves were applied, and repeated until reaching a stabilization of the transvalvular gradient for 3 consecutive sequences. The therapy device was controlled by a 3-axis motor for scanning the ultrasounds continuously and uniformly over the entire valve.

In order to assess the modification of the biomechanical properties induced by the application of ultrasound focused waves, shear wave elastography, an ultrasound-based tool for noninvasive evaluation of soft tissue's stiffness, was used. The Aixplorer ultrasound imaging system (Aixplorer™, Supersonic Imagine, Aix-en-Provence, France) with a linear probe (SL10-2) was used to evaluate the stiffness of each valvular leaflet. Three acquisitions were made for each leaflet, using the shear wave elastography imaging mode (SWE™) of the Aixplorer scanner in the 'penetration' setting. A "QBox™" region of interest (mean diameter 1 mm) was positioned inside the elasticity image after each acquisition to obtain a mean stiffness value.

Figure 6:
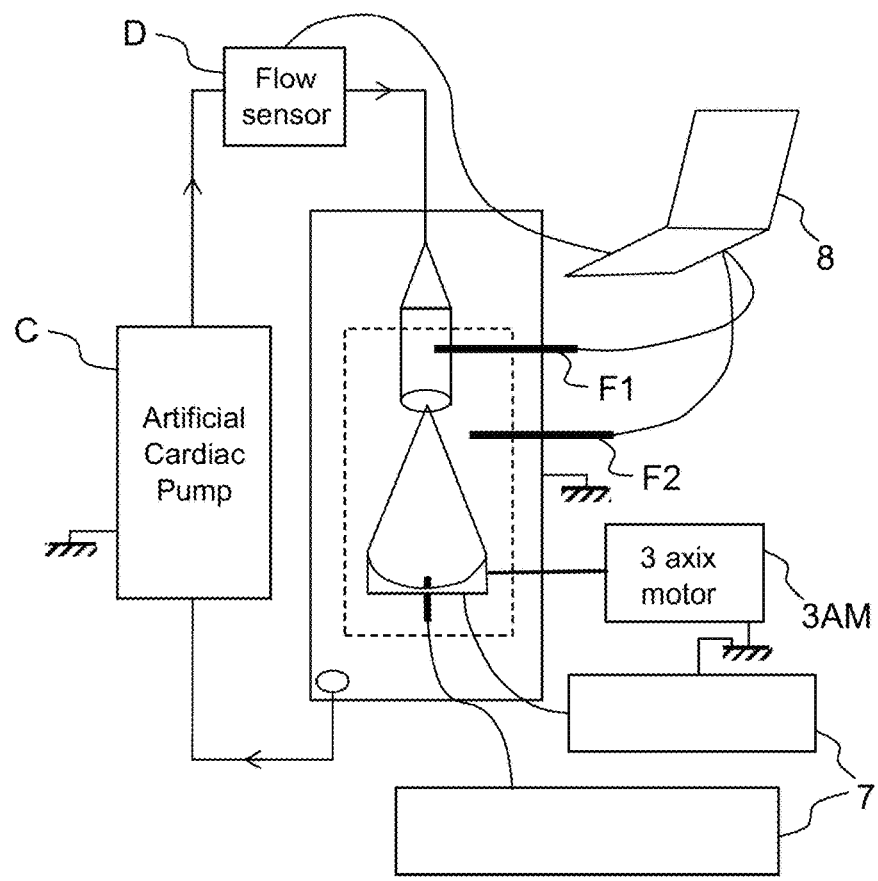
FIG. 6 illustrates an experimental setup for testing the inventive method in vitro.

The setup of the in vitro procedure is illustrated on FIG. 6. A bioprothesis A is placed right in front to the therapy device B, including transducer 6 and imaging probe 4, both immersed in degassed water. A three-axes motor 3AM was used to adjust the position of the therapy device 6. An artificial cardiac pump C (Harvard Apparatus Pulsatile Blood Pump®) induced a pulsatile flow through the valve. The flow rates were applied at 3 L, 4 L and 5 L per minute, monitored by a flow sensor D (Small flow Meter Kit, Atlas Scientific®; accuracy +/−1 ml/min). water. The transvalvular pressure gradient was estimated by:

- A continuous Doppler ultrasound assessment by applying the Bernoulli equation [$\Delta P=4(V_{max})^2$]
- Hemodynamic assessment by pressure sensor before (reference F1) and after (reference F2) the valve (sensor IXIAN™ 0-7.5 PSI Industrial Control Pressure Sensor, Atlas Scientific®; accuracy +/−1 mmHg)

The pump operated during 2 hours at 4 L/min flow rate (70 cycles per minute, ejection volume equal to 57 mL) to control the variation of the gradient before carrying out the inventive method, after which sequences of ultrasound focused waves were applied.

After the procedure, Elastography was performed again on each valve.

Finally, the bioprostheses were sent to the department of pathology of Hopital Europeen Georges Pompidou (Paris) for histopathological analysis.

For carrying out the in vivo procedures, bioprostheses explanted on humans, of the same type as those used in the in-vitro procedure, were implanted on sheep.

Figure 7:
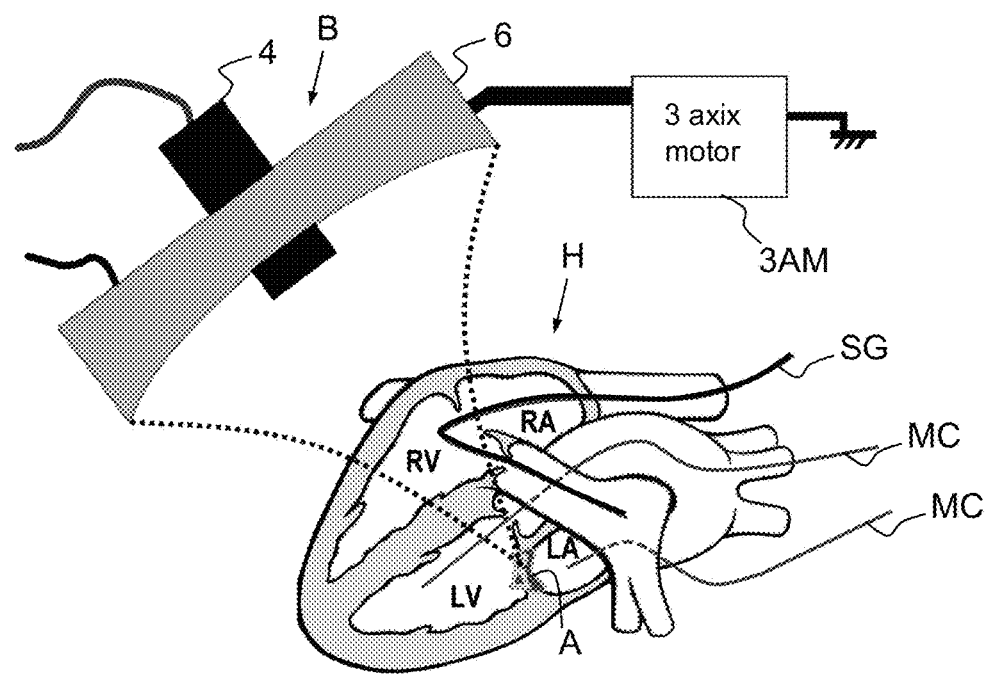
FIG. 7 illustrates an experimental setup for testing the inventive method in vivo.

The implantation was performed in mitral position, and not in aortic position, because of the relative diameters of the implanted valves and of the sheep's aortic valves (diameter between 8 and 16 mm). The inventors consider that the mitral implantation was acceptable to determinate if the application of focused ultrasound waves could decrease the calcified stenosis. The setup is illustrated on FIG. 7.

Elastography of the bioprosthesis was done before and after each procedure. The animal procedure was approved by the Institutional Animal Care and Use Committee of Hopital Europeen Georges Pompidou (PARCC) according to the European Commission guiding principles (2010/63/EU).

The sheep were anesthetized with thiopentothal (0.5 m L/kg), intubated, ventilated at 15 mL/kg with 2% isoflurane, and given glycopyrrolate (0.4 mg intravenous) and vancomycin (0.5 grams intravenous). A sterile sternotomy was performed. The calcified bioprosthesis was implanted in mitral position, after CPB. Vital signs (including heart rate (HR), oxygen saturation, arterial blood pressure (BP)), left atrial and ventricle pressure (by two Mikro-Tip® Millar Catheter Transducers MC, to have the transvalvular pressure gradient in real time) and cardiac flow (by a Swan-Ganz CCOmbo Pulmonary Artery Catheter, Edwards Lifesciences®, reference SG) were monitored. The CPB was stopped and removed to restore independent cardiac activity. Sternotomy was maintained and the thorax was filled with degassed saline water. A completed echocardiography was realized, especially to evaluate the calcified bioprosthesis.

The therapy device B was immersed in the water filling the thorax and positioned near the heart H (RA: right atrium, LA: left atrium; RV: right ventricle; LV: left ventricle) with the help of a three-axis motor 3AM in order to apply several sequences of focused ultrasound waves onto the implanted bioprothesis A. An echocardiographic evaluation was realized between each sequence, in parallel of the catheters evaluation (pressure and cardiac flow).

At the end of the procedure, the animal was sacrificed (Dolethal™ intravenous injection, 1 ml/kg) and an anatomical macroscopic evaluation of the cardiac structure was performed. The bioprosthesis was then explanted and sent after elastography to the department of pathology for histopathological analysis.

Immediately after the procedure (in vitro and in vivo), the bioprosthesis were dissected, fixed in formalin and embedded in individual paraffin blocks. Regions of interest, like macroscopic calcification on leaflet, were labeled with tattoo ink. Serial sections were stained with H&E (hematoxylin and eosin) for histopathological analysis.

In addition, 5 calcified bioprostheses were also sent for histopathological analysis directly after their explantation from human, without any application of ultrasound. The objective was to allow a histopathological comparison between bioprostheses with or without treatement.

Results are presented and discussed belows. Continuous variables are presented as mean±standard deviation (SD) or median with minimum and maximum range, and categorical variables are presented as percentage±95% CI. Comparisons of categorical variables were made using chi-square test, or Fisher exact test when appropriate. Univariate analyses of continuous variables were performed with the paired two-tailed Student's t-test (normal distribution). Univariate comparisons for categorical variables were performed with the two-tailed $\chi^2$ test or, when necessary (one or more of the cells have an expected frequency of five or less), the Fisher's exact test. The level of significance was set at an alpha level of 0.05 or less. Analysis was conducted using Medcalc™ (MedCalc Software, Mariakerke, Belgium).

All the results show a softening of the valve leaflets allowing a decrease of the anterograde gradient. This decrease is persistent one month after the treatment. The decrease of transvalvular gradient measured by Doppler echocardiography was confirmed by invasive pressure sensors in both in vitro and in vivo setup.

Figure 8:
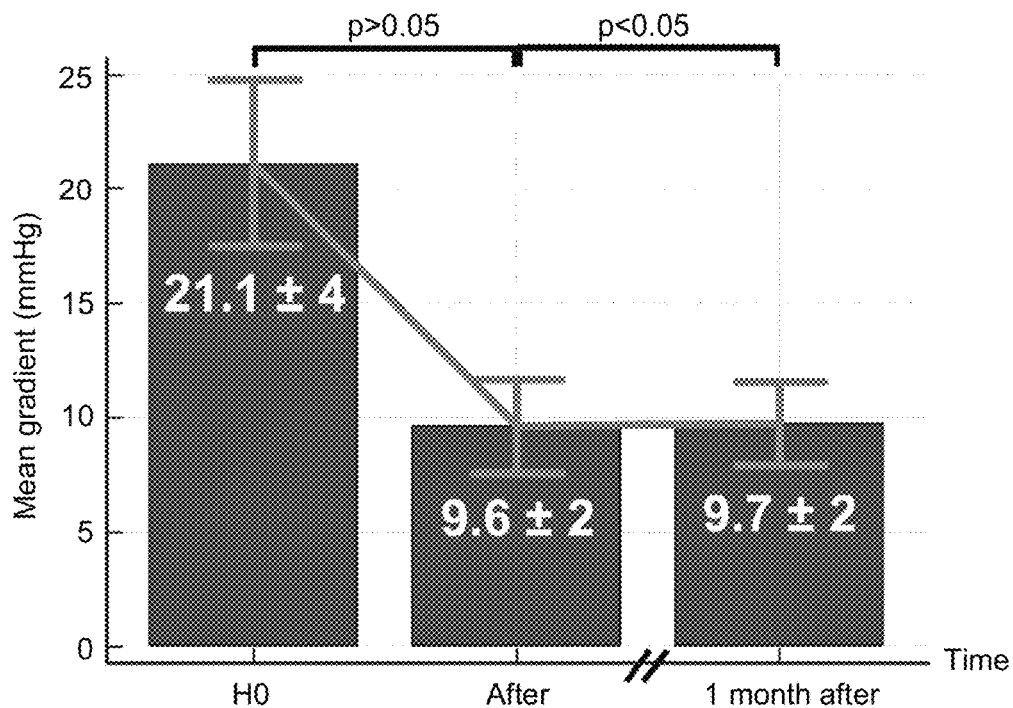
FIGS. 8, 9 and 10 are plots of transvalvular gradients measured in vitro after performing the inventive method.

FIG. 8 illustrates results obtained for the in vitro procedure. Eight bioprostheses were explanted and used for this procedure. At a flow rate of 4 L/min, the mean transvalvular gradient over the set of valves was 21.1±3.9 mmHg (max=38, min=10, FIG. 8, H0) and the maximum gradient was 39±6.9 mmHg (max=73, min=22). After two hours (H2) of controlled pulsatile flow, no statistically significant change of the transvalvular gradients was observed. The mean duration of the treatment was 70±12 minutes with a maximum duration of 90 minutes and a minimum of 50 minutes. The pump flow was adjusted to maintain a constant flow of 4 L/min during and after the treatment. After the procedure, the mean transvalvular gradient was 9.6±1.7 mmHg (max=19; min=4), which corresponds to a decrease of 55±10% (p<0.01) and the maximum gradient was 19.6±3.5 mmHg (max=37; min=10), which corresponds to a decrease of 51±9% (p<0.01).

Hemodynamic parameters were also measured at 3 L/min and at 5 L/min, before and after procedure, and the gradients also showed a significant decrease (p<0.01). At 3 L/min, the mean gradient varies from 14.2±2.5 to 7.1±1.2 mmHg (p<0.01) and the maximum gradient from 29.1±5.1 to 14.9±2.6 mmHg (p<0.01). At 5 L/min, the mean gradient varies from 23.8±4.2 to 13±2.3 mmHg (p<0.01) and the maximum gradient from 42.3±7.5 to 24.1±4.3 mmHg (p<0.01).

All post-treatment transvalvular gradients were re-assessed one month after the procedure and there was no statistically significant difference (FIG. 8).

Figure 9:
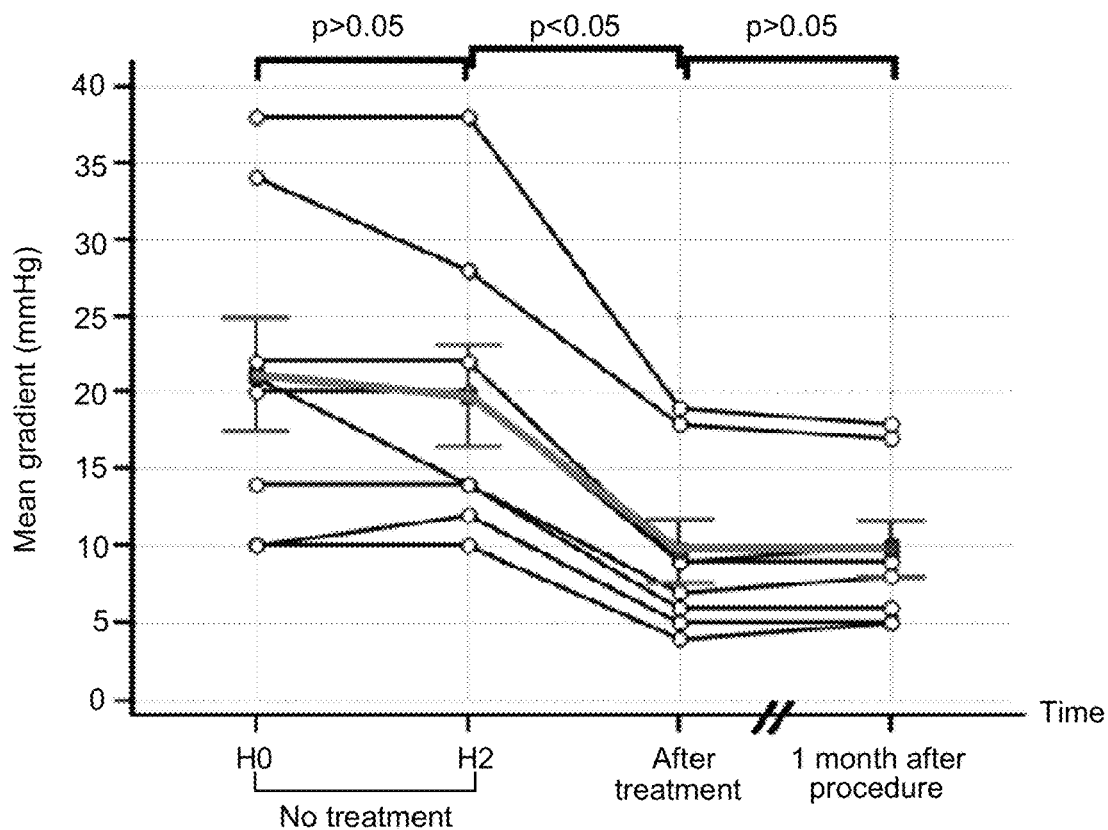
Figure 10:
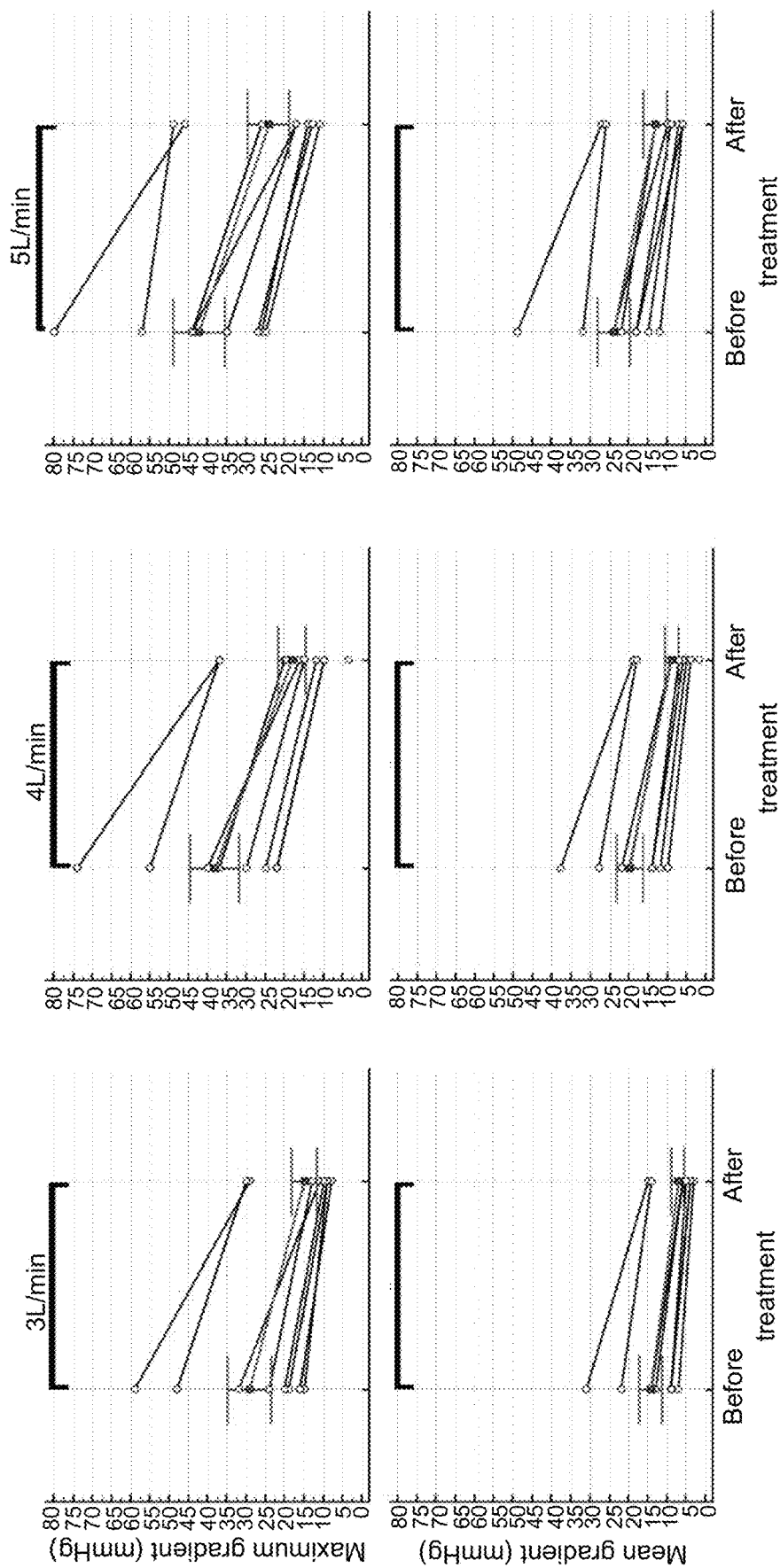

FIG. 9 shows mean transvalvular gradient results for each valve treated in vitro. FIG. 10 shows multi flow results (3 L, 4 L and 5 L/min) obtained in vitro for each valve.

Figure 11:
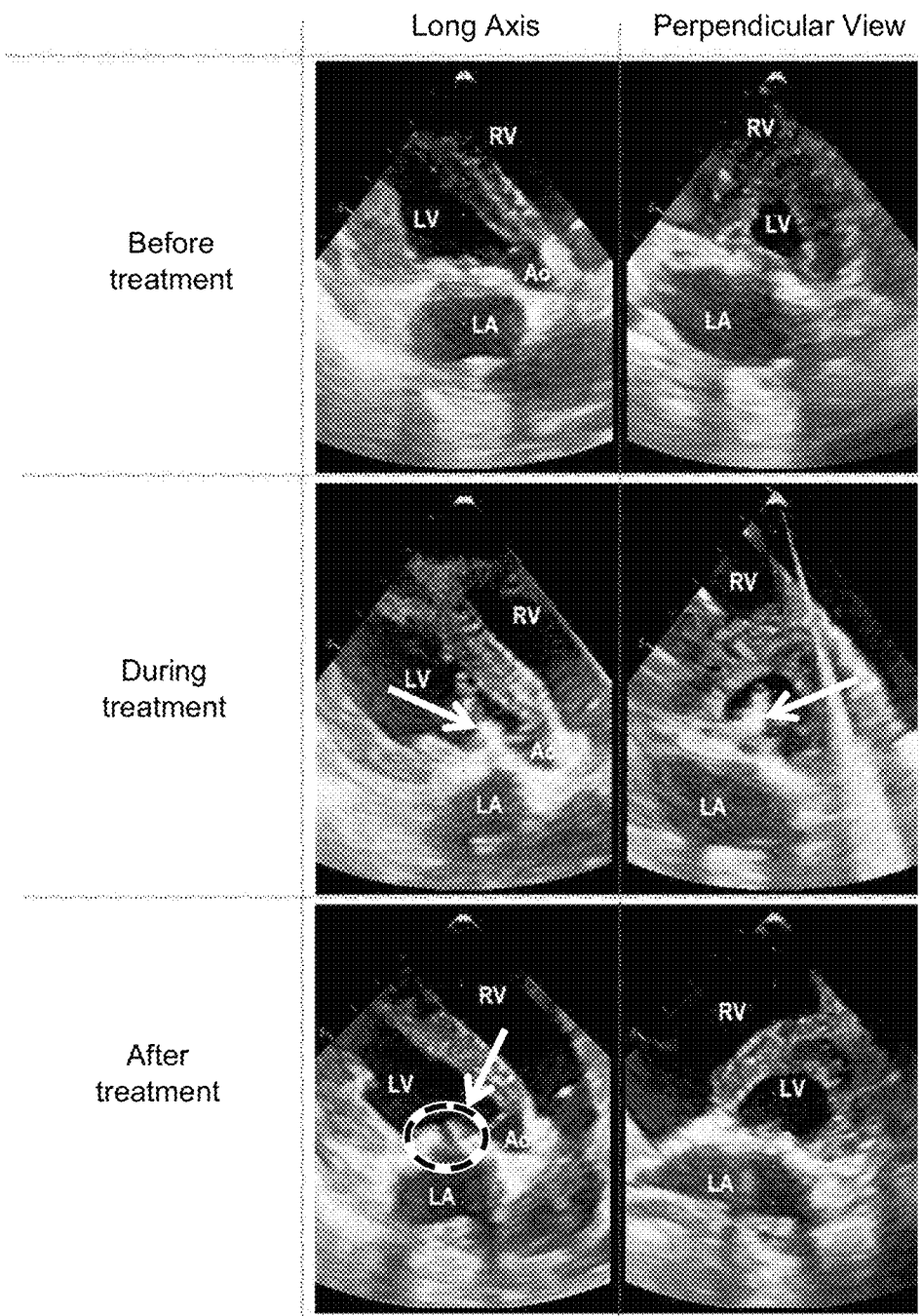
FIG. 11 shows echocardiography images acquired in vivo before, during and after applying the inventive method.
Figure 12:
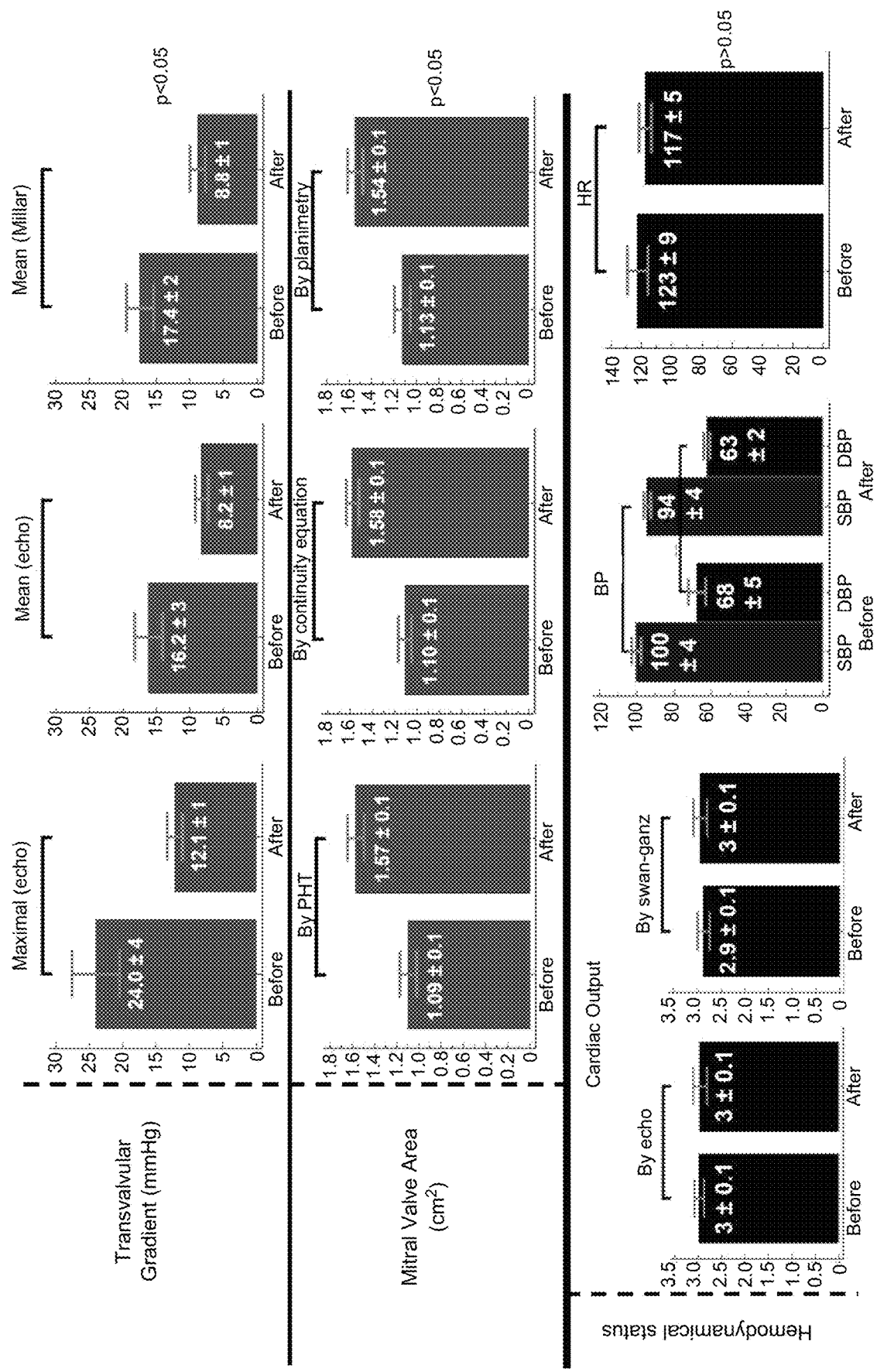
FIG. 12 shows experimental results obtained in vivo.

Results for in vivo procedure are reported in table 1 and illustrated by FIGS. 11 and 12.

Fourteen explanted bioprostheses were used for this procedure. Seven of the animals suffered a massive acute pulmonary edema with severe heart failure, just after the implantation of the valve and the cessation of the CPB. These animals died before the procedure. The other animals tolerated the implantation, seven valves were thus treated and analyzed.

The mean weight of the animals was 37.8±4.6 kg (min=29; max=43).

Just after the valve implantation, all the parameters were monitored for one hour, before any treatment, and there was no statistically significant change of the transvalvular gradients (p=0.45) and mitral valve areas (planimetry, p=0.38; continuity equation, p=0.74; PHT, p=0.51).

The mean duration of procedure was 60±13 minutes with a maximum duration of 100 minutes and a minimum of 40 minutes. An important decrease of the transvalvular gradient was observed after treatment (see table 1). The mean cardiac frequency was 123±9 (min=94; max=154) and all the hemodynamic parameters were stable during the procedures: HR (p=0.24), BP (p=0.27), O2 saturation (p=0.42). The results of elastography, of echocardiography and of pressure/flow cardiac catheters of the procedures are synthesized in the table 1 and illustrated on FIG. 12.

FIG. 11 shows echocardiography images acquired before, during and after the treatment. During the treatment, the "cloud of cavitation" (microbubble) is visible, and highlighted by an arrow. After treatment, the modification of the bioprothesis opening is confirmed by echocardiography (see the arrow on the lowest-leftmost image of the figure).

No mitral valve regurgitation was observed at the end of procedures.

Isolated ventricular extrasystols (VES) was observed in two animals, without any repercution on hemodynamic parameters. As long as the focal spot of the therapy device remained at the bioprosthesis, no arrhythmia was visible.

Macroscopic analysis of hearths explanted after euthanasia of the animals showed all cardiac structures were intact, except in one animal in which a superficial hematoma (epicardium) of 7 mm diameter was visible at the lateral LV wall (on the path of the ultrasound beam). This animal was also one of two animals who presented isolated VES.

At the end, the bioprothesis was sent to the department of pathology for histopathological analysis.

TABLE 1

| In vivo results | | | | |
|---|---|---|---|---|
| | Before Treateement | After Treateement | Variation Before/ After (%) | P |
| Shear Wave Imaging | | | | |
| Elastography (kPa) | 76.1 ± 23.7 | 35.6 ± 7.2 | 52 ± 7 | 0.0009 |
| Echocardiography | | | | |
| Doppler Mitral Valve | | | | |
| Maximal Velocity (m/s) | 2.41 ± 0.50 | 1.73 ± 0.21 | 28 ± 6 | 0.007 |
| Maximal Pressure Gradient (mmHg) | 24.0 ± 4.4 | 12.1 ± 1.4 | 49 ± 11 | 0.003 |
| Mean Velocity (m/s) | 1.95 ± 0.36 | 1.38 ± 0.24 | 29 ± 6 | 0.001 |
| Mean Pressure Gradient (mmHg) | 16.2 ± 3.2 | 8.2 ± 1.3 | 48 ± 7 | 0.0006 |
| Mitral Valve Area (cm$^2$) | | | | |
| By pressure half time (PHT, FIG. 5B) | 1.09 ± 0.09 | 1.57 ± 0.08 | 143 ± 18 | 0.0001 |
| By continuity equation | 1.10 ± 0.15 | 1.58 ± 0.15 | 142 ± 15 | 0.0001 |
| By planimetry | 1.13 ± 0.13 | 1.54 ± 0.14 | 137 ± 14 | 0.0001 |
| Pulmonary artery pressure (mmHg) | | | | |
| Maximal (Tricuspid Valve) | 64.7 ± 12.8 | 34.1 ± 10.2 | 47 ± 12 | 0.0002 |
| Cardiac Output* (L/min) | 2.98 ± 0.1 | 2.96 ± 0.14 | 1 ± 0.2 | 0.83 |
| Pressure Captors (Millar) (mmHg) | | | | |
| Mean Diastolic Left Atrium (LA) | 36.8 ± 6.2 | 20.2 ± 5.1 | 44 ± 11 | 0.004 |

TABLE 1-continued

In vivo results

| | Before Treatement | After Treatement | Variation Before/ After (%) | P |
|---|---|---|---|---|
| Mean Diastolic Left Ventricle (LV) | 17.4 ± 2.7 | 11.4 ± 1.9 | 35 ± 10 | 0.014 |
| Mean Diastolic Gradient LV-LA | 17.4 ± 2.4 | 8.8 ± 1.2 | 50 ± 13 | 0.002 |
| Cardiac Flow Captor (L/min) | | | | |
| Swan-Ganz catheter | 2.87 ± 0.11 | 2.96 ± 0.14 | 3 ± 0.4 | 0.74 |

± SD
* Cardiac Output = HR × LVOT area × LVOT VTI

In vitro, before the treatment, the mean stiffness of the valves leaflets measured by elastography was 105.8±9 kPa. After the procedure, the mean stiffness of valves leaflets measured by elastography was 46.6±4 kPa. It corresponds to a decrease of 55±8% (p<0.01).

Figure 13:
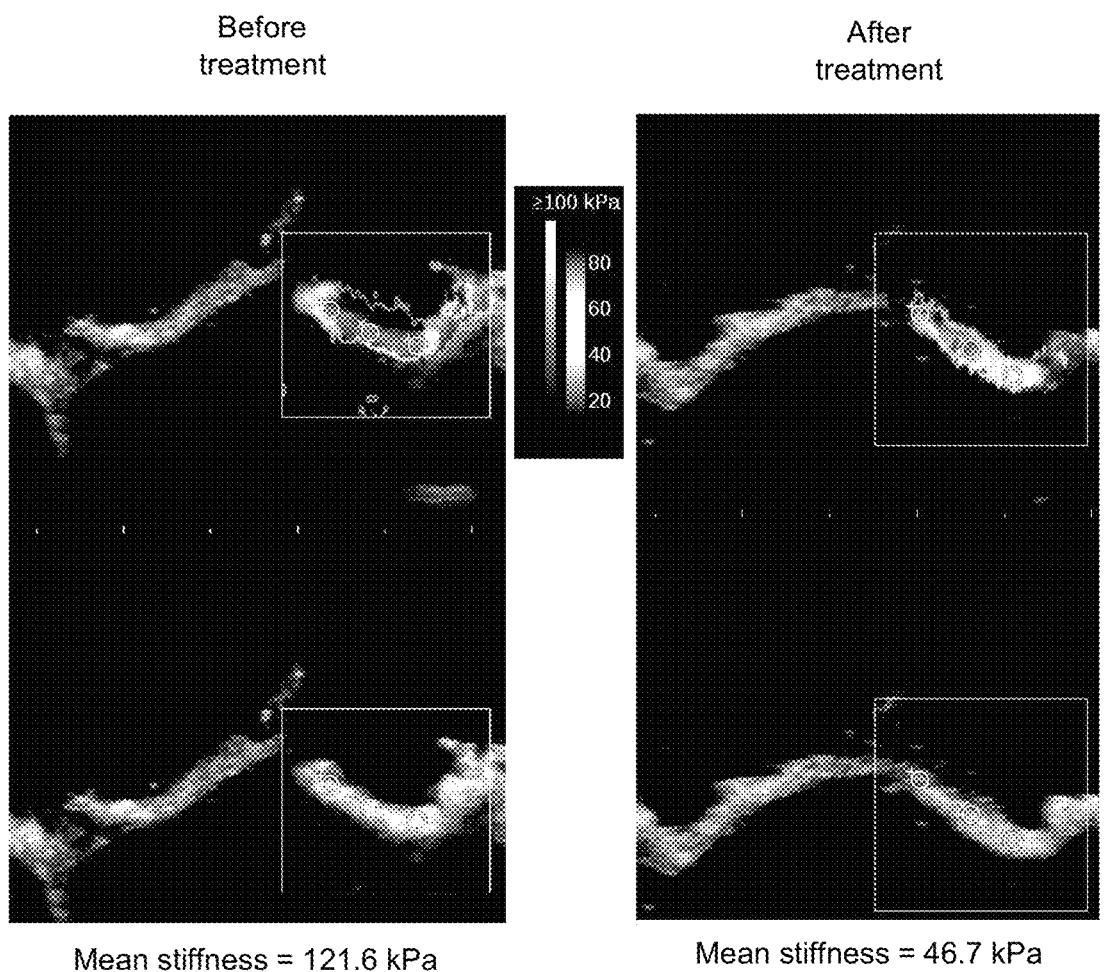
FIGS. 13 to 15 illustrate the stiffness reduction of bioprostheses submitted to the inventive method, measured by Shear Wave Elastography.
Figure 14:
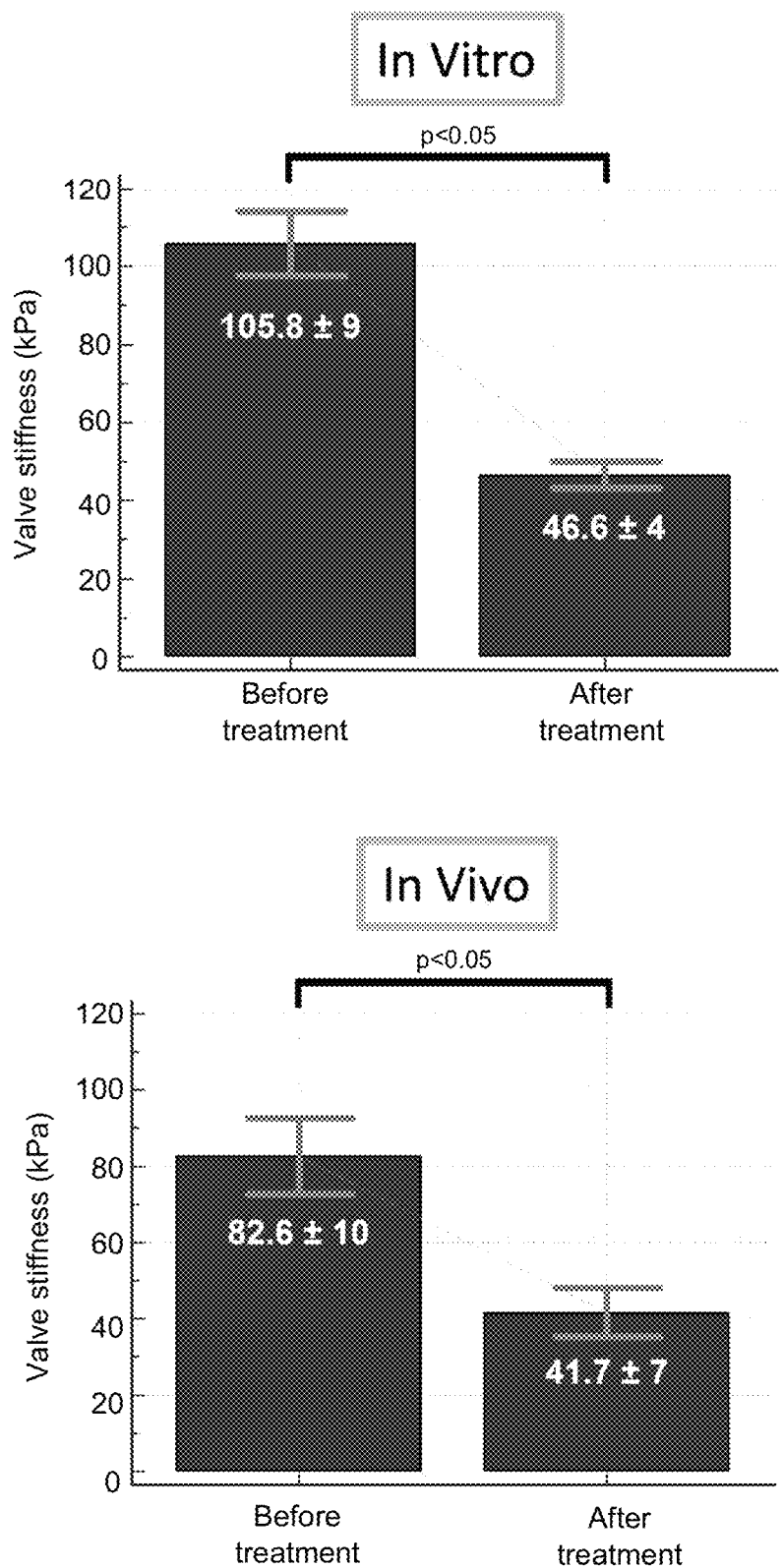
Figure 15:
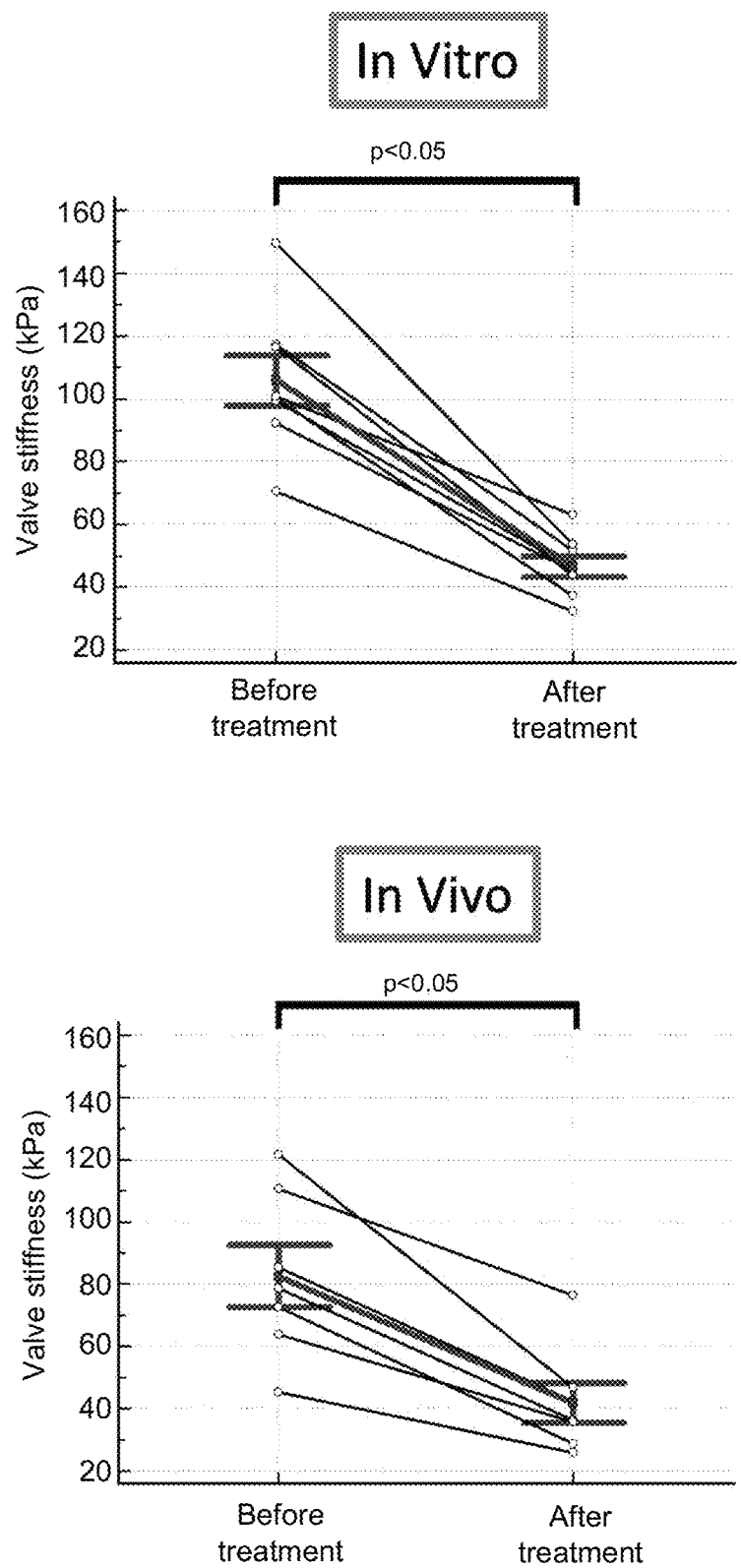

A similar stiffness decrease was observed for the bioprosthesis used in vivo (82.6±10 kPa before the procedure and 41.7±7 kPa after the treatment, 49±7% decrease, p<0.01). FIG. 13 shows exemplary Shear Wave Elastography images acquired in vitro to measure mean stiffness. FIG. 14 shows numerical results obtained in vitro (upper panel) and in vivo (lower panel). Stiffness results for each individual bioprosthesis are shown on FIG. 15.

Figure 16:
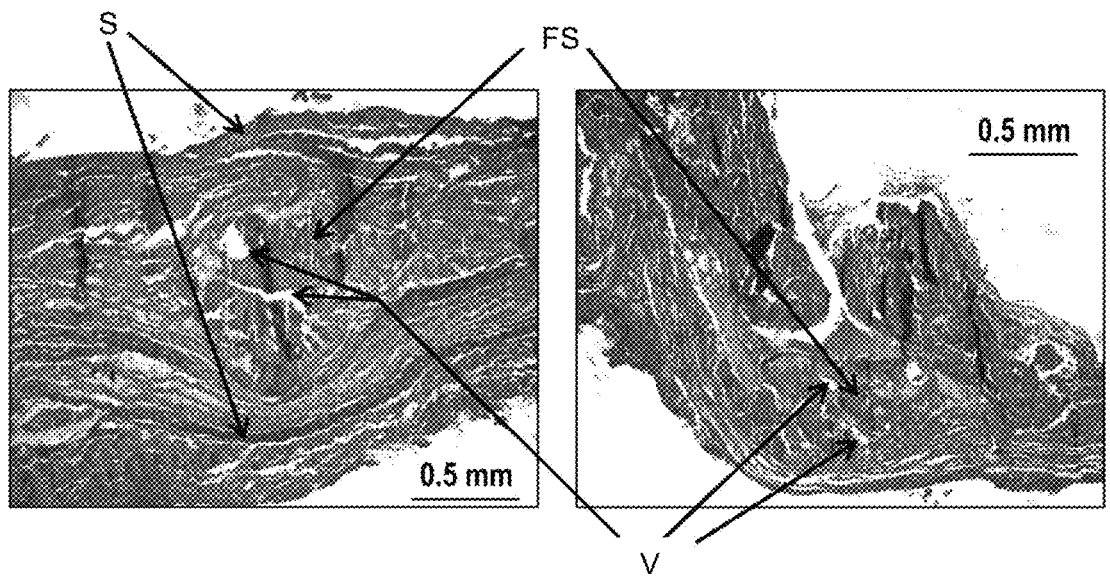
FIG. 16 shows histological samples of human calcified aortic bioprostheses submitted to the inventive methods and shows the effects of the inventive methods on calcifications.

FIG. 16 shows histological images of a treated bioprosthesis. All the superficial structures of the leaflets (fibrosa and ventricularis) were intact—see reference S. In comparison with the five bioprostheses explanted without application of the procedure, it was possible to observe:

A fragmentation and a "siping" of the calcification—see reference FS.
Presence of vacuoles (reference V) inside the calcification
There was no histological evidence for acute inflammation or acute thrombosis on the bioprosthesis.
Similar results are observed on native valves.

The experimental results show that, after the treatment, the mean and maximal transvalvular gradients were decreased by two-fold both in vitro and in vivo. Moreover, these hemodynamical modifications persisted after one month (in vitro procedure). The evolution of other echocardiographic parameters measured in vivo (valve area, PAP) confirmed the decrease of the valvular stenosis. Finally, it was shown that the treatment induced a decrease of the valves leaflet stiffness.

There was no statistical difference between the duration of the in vitro (70±12 minutes) and in vivo (60±13 minutes) procedures (p=0.33).

Additional tests were performed to determine whether the stiffness reduction induced by the treatment results from softening of the valve tissues, fragmentation and cracking of the calcifications or both.

Figure 17:
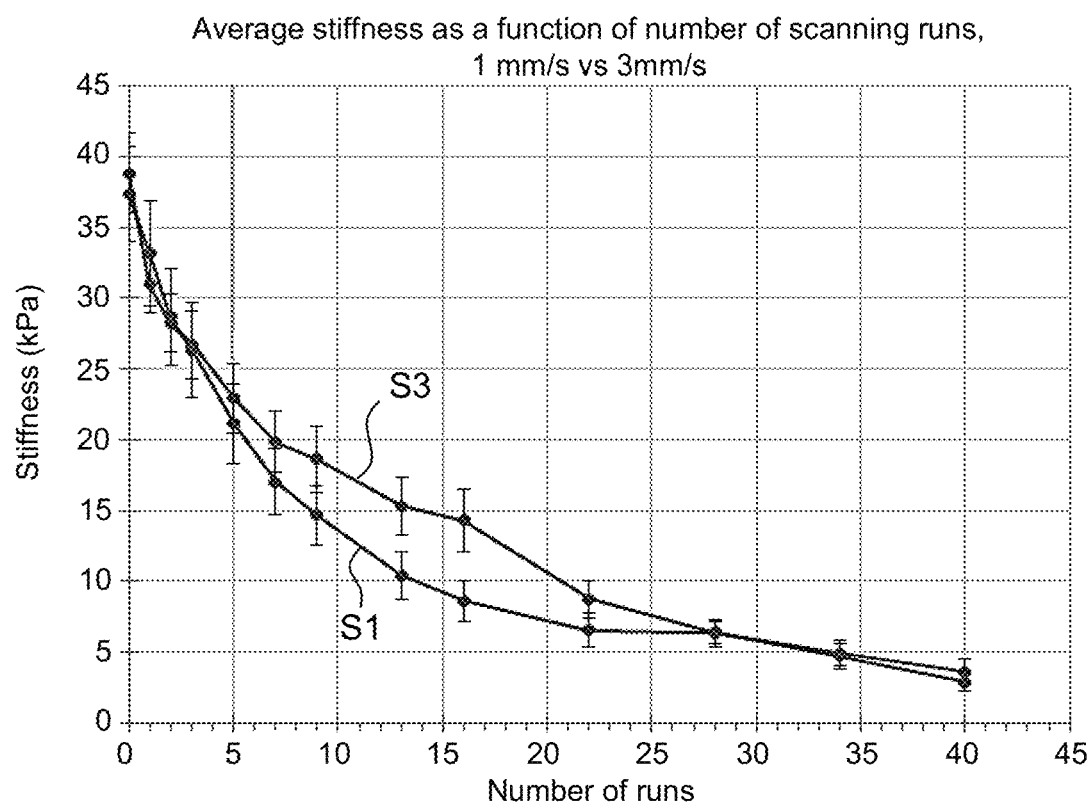
FIG. 17 illustrates the effects of the inventive methods on porcine pericardium.

In order to assess the effect of focused ultrasound waves on the valvular tissue, tests were performed using detergent-decellularized porcine pericardium, which is a suitable model. Ultrasound focused waves at 1.25 MHz, 8 cycles/pulse (6.4 microseconds), where emitted at a repetition rate of 100 Hz and steered to scan the pericardium sample at two different speeds, 1 mm/s and 3 mm/s. Scanning was performed along three parallel lines, run through in two opposite directions. The pericardium stiffness was measured by elastography at three different spots. FIG. 17 shows the evolution of the average stiffness with the number of runs at a scanning speed of 1 mm/s (curve 51) and 3 mm/s (curve S3). Taking into account the fact that a run at 1 mm/s takes three times longer than at 3 mm/s, it can be seen that stiffness decreases faster at 3 mm/s, but in both cases a five-fold stiffness reduction is achieved. Perforation is achieved at 40 runs, independently from the scanning speed.

In order to assess the effect of focused ultrasound waves on calcifications, tests were performed on formaldehyde-fixed calcified human aortic valves. The samples were treated in hydraulic bench with a 1 MHz transducer at an emission frequency of 1.25 MHz, a pulse repetition frequency of 100 Hz and 8 cycles. The power level was set at a level necessary to observe cavitation and the saline was degassed to below 1 mg/L of O2. The cusps were placed on an absorber with needles with the fibrosa facing the transducer. The samples were moved in the X and Y direction with a "snake" pattern to treat the chosen area with a speed of 1 mm/s.

In order to perform Micro-CT image acquisition, the cusps of the valves were placed in saline in a plastic tube cap and imaged with a field of view of 10 mm (FOV10) and a voxel size of 20 µm. Software was used to attempt to re-align slices of stacks taken before and after treatment. The results are only qualitative so far; however, there seems to be a fragmentation and cracking of the calcifications following ultrasonic treatment of the cusps.

It can then be inferred that the stiffness reduction induced by the treatment results from both softening of the valve tissues and fragmentation of the calcifications.

The results above suggest that pulsed cavitational focused ultrasound can have a real clinical impact on calcified valves and can be considered as a new therapeutic strategy. Its two main advantages are that it could theoretically be applied totally noninvasively and would allow the preservation of the native valve ad intergrum.

Another challenge for our in vivo study is the accuracy of the treatment that will allow to have a safe procedure. For a few animals indeed (two animals) a few non persistent ventricular extrasystoles were observed, and post mortem anatomic exploration showed bruising of the cardiac wall, due to off target cavitation. These two undesirable effects are mostly induced by the inaccuracy of the target positioning and motion and could be greatly reduced by tracking the valve motion, as explained above. This will be even more important in actual non-invasive implementations, wherein the therapy transducer will be much farther away from the valve than in the setup of FIG. 7.

An alternative or complementary solution would be to trigger histotripsy exposures by electrocardiogram. Indeed, it is possible to select specific moments in the cardiac cycle for example during the refractory period of the myocardium (to avoid inducing extrasystoles) or when the aortic valve is closed and thus its whole surface is equally exposed, and far away from the cardiac wall.

Figure 18:
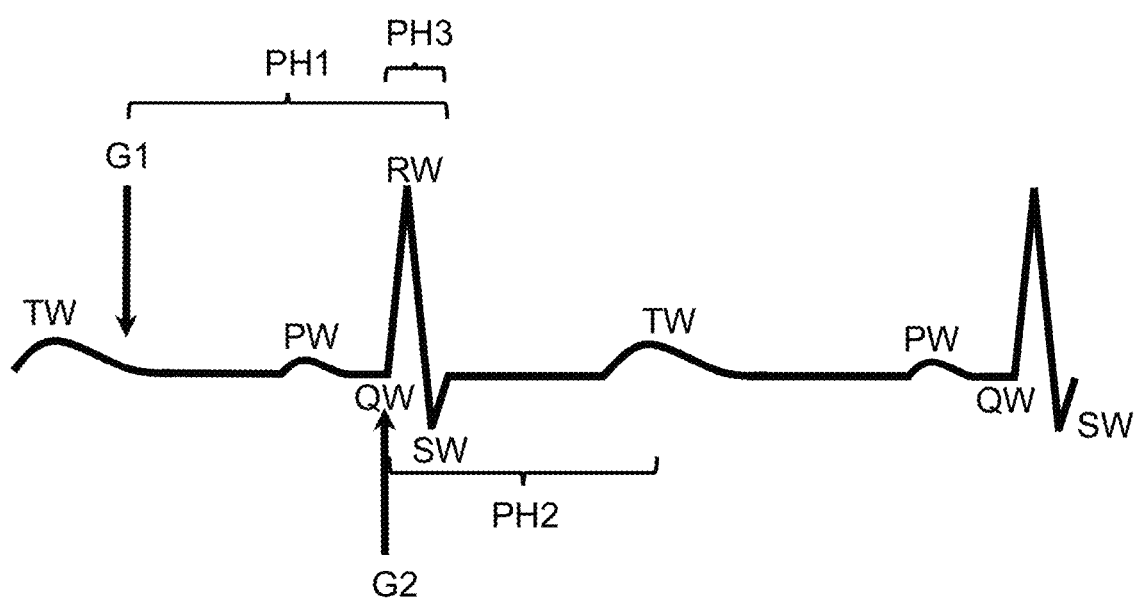
FIG. 18 illustrates the use of ECG gating in a method according to an embodiment of the invention.

FIG. 18 is a simplified representation of an electrocardiographic trace; references TW, PW, QW, RW, SW correspond to T-waves, P-waves, Q-waves, R-waves and S-waves respectively; G1 and G2 correspond to suitable gating time, i.e. start times for ultrasound pulses; PH1, PH2 and PH3 identify time periods during which ultrasound pulses may be applied with optimal safety and/or effectiveness.

The first period, PH1, starts at G1, after the T-wave, and ends after the R-wave; it has duration of about 650 ms. It corresponds to the period when the aortic valve is closed.

The second period, PH2, starts at G2 (i.e. on the R-wave) and ends at the T-wave; it has duration of about 250 ms. It corresponds to a refractory period of the heart, where the risk of inducing extrasystoles is minimal, and therefore safety is maximal.

The third period, PH3, is the intersection of PH1 and PH2. It starts at G2 and has duration of about 30 ms. It corresponds to optimal conditions: the aortic valve is closed, and the hearth is in its refractory period. Its main drawback is its short duration (30 ms/cycle).

ABBREVIATIONS

BP: blood pressure
CBP: cardiopulmonary bypass
CI: confidence interval
CUSA: cavitron ultrasonic surgical aspirator
HIFU: high intensity focused ultrasound
HR: heart rate
LVOT: left ventricle outflow tract
PHT: pressure half time
PMV: percutaneous balloon mitral valvuloplasty
PRF: pulse repetition frequency
SD: standard deviation
SEM: standard error of mean
SWE: shear wave elastography
VTI: velocity time integral

The invention claimed is:

1. An apparatus for treating or preventing valvular stenosis, said apparatus comprising:
   an ultrasound probe located externally to a heart of patient, able to produce ultrasound waves focused inside said heart and suitable to generate, at a focal spot, a pressure sufficient to result in cavitation,
   an imaging device for mapping in real time a treatment region of a cardiac valve of the patient, said treatment region comprising at least one leaflet of the cardiac valve,
   a controller configured for driving the ultrasound probe to emit a sequence of focused ultrasound waves in such a way that a duration of a pressure pulse generated by each focused ultrasound wave of the sequence of focused ultrasound waves is less than 80 microseconds, and in such a way that each of them generates at a focal spot a peak negative pressure half-cycle that exceeds a peak negative pressure of 5 MPa and/or a peak positive pressure half-cycle that exceeds a peak positive pressure of 10 MPa,
   the controller being further configured for estimating in real-time a motion of the treatment region from images acquired by said imaging device, and for steering the focused ultrasound waves emitted by the ultrasound probe in function of said motion of the treatment region to scan the entire treatment region;
   the apparatus further comprising a measuring device suitable for measuring an index of valvular stenosis after having controlled the ultrasound probe to emit the sequence of N focused ultrasound waves, the controller being further configured for reiterating the steps of controlling the ultrasound probe to emit a sequence of focused ultrasound waves and measuring said index of valvular stenosis until said index crosses a predefined threshold.

2. The apparatus according to claim 1, further comprising a robotic arm carrying said ultrasound probe, the controller being configured for driving the robotic harm to control the location of the ultrasound probe externally to the heart of the patient so as to keep the treatment region inside a scannable region of the ultrasound probe.

3. The apparatus according to claim 1, wherein said measuring device is a Doppler imager configured for measuring a hemodynamic parameter, said index of valvular stenosis being a function of said hemodynamic parameter.

4. The apparatus according to claim 1, wherein said measuring device is an imaging device configured for detecting and estimating a valve motion parameter, said index of valvular stenosis being a function of said valve motion parameter.

5. The apparatus according to claim 1, wherein said measuring device is a shear wave imager configured for measuring a shear wave propagation parameter, said index of valvular stenosis being a function of said shear wave propagation parameter.

6. The apparatus according to claim 1, wherein the controller is configured for driving the ultrasound probe to emit said sequence of focused ultrasound waves at a rate between 20 and 5000 shots per seconds.

7. The apparatus according to claim 1, wherein the controller is configured for steering the focused ultrasound waves so as to move their focal spot at a travelling speed comprised between 0.1 mm/s and 10 mm/s.

8. The apparatus according to claim 1, wherein the controller is configured for steering the focused ultrasound waves in such a way that a point of the treatment region is included in the focal spots of a number M of focused ultrasound waves of the sequence of focused ultrasound waves, said number M being comprised between 1 and 1000, preferably between 2 and 1000, even more preferably between 15 and 150.

9. The apparatus according to claim 1, wherein the controller is configured for steering the focused ultrasound waves in such a way that the focal spots of the sequence of focused ultrasound waves are separated from one another by a minimal distance larger than 0.1 millimetres.

10. The apparatus according to claim 1, wherein the controller is configured for driving the ultrasound probe in such a way that a duration of a pressure pulse generated by each focused ultrasound wave of the sequence of focused ultrasound waves is less than 20 microseconds.

11. The apparatus according to claim 1, wherein the ultrasound probe comprises a plurality of transducers within a reflective cavity, and wherein the controller is configured for driving at least one said transducer to emit an emission signal in the reflective cavity, the duration of said emission signal being less than 10 milliseconds, preferably less than 1 millisecond.

12. The apparatus according to claim 1, wherein the controller is further configured for receiving an electrocadiography signal and for driving the ultrasound probe to emit the sequence of focused ultrasound waves during specific moments in a cardiac cycle, determined from said electrocardiography signal.

13. A method for treating or preventing valvular stenosis comprising: providing an ultrasound probe located externally to a heart of a patient and able to produce ultrasound waves focused inside said heart, mapping a treatment region of a cardiac valve of the patient, said treatment region comprising at least one leaflet of the cardiac valve, controlling the ultrasound probe to emit a sequence of N focused ultrasound waves, wherein each focused ultrasound wave of the sequence of N focused ultrasound waves generates a pressure sufficient to result in cavitation at a focal spot of said focused ultrasound wave, wherein the focal spots of the sequence of N focused ultrasound waves scan the entire treatment region to soften the tissues of the treatment region; wherein the duration of a pressure pulse generated by each focused ultrasound wave of the sequence of focused ultrasound waves is less than 80 microseconds, and wherein each focused ultrasound wave of the sequence of focused ultrasound waves generates at a focal spot a peak negative pressure half-cycle that exceeds a peak negative pressure of 5 MPa and/or a peak positive pressure half-cycle that exceeds a peak positive pressure of 10 MPa.

14. The method according to claim 13, wherein said step of controlling the ultrasound probe to emit a sequence of N focused ultrasound waves comprises: emitting the sequence of focused ultrasound waves at a predefined rate of emission, and moving the focal spot of the focused ultrasound waves to scan the entire treatment region.

15. The method according to claim 13, wherein said predefined rate of emission is comprised between 20 and 5000 shots per seconds.

16. The method according to claim 14, wherein the focal spot of the focused ultrasound waves is moved with a predefined travelling speed, said predefined travelling speed being comprised between 0.1 mm/s and 10 mm/s.

17. The method according to claim 13, wherein the focused ultrasound waves emitted by the ultrasound probe are steered to scan the entire treatment region.

18. The method according to claim 17, wherein the sequence of N focused ultrasound waves is such that a point of the treatment region is included in the focal spots of a number M of focused ultrasound waves of the sequence of focused ultrasound waves, said number M being comprised between 1 and 1000.

19. The method according to claim 18, wherein the sequence of N focused ultrasound waves is such that a point of the treatment region is included in the focal spots of a number M of focused ultrasound waves of the sequence of focused ultrasound waves, said number M being comprised between 15 and 150.

20. The method according to claim 13, wherein the focal spots of the sequence of focused ultrasound waves are separated from one another by a minimal distance larger than 0.1 millimetres.

21. The method according to claim 13, wherein the treatment region covers a surface of at least 9 square millimetres, measured in a plane perpendicular to an opening direction of the cardiac valve.

22. The method according to claim 13, further comprising: measuring an index of valvular stenosis after having controlled the ultrasound probe to emit the sequence of N focused ultrasound waves, and, until said index crosses a predefined threshold, reiterating the steps of controlling the ultrasound probe to emit a sequence of N focused ultrasound waves and measuring said index of valvular stenosis.

23. The method according to claim 22, wherein said index of valvular stenosis is function of a hemodynamic parameter and the step of measuring said index of valvular stenosis comprises Doppler imaging.

24. The method according to claim 22, wherein said index of valvular stenosis is function of a valve motion parameter and the step of measuring said index of valvular stenosis comprises estimation of valve motion.

25. The method according to claim 22, wherein said index of valvular stenosis is function of a shear wave propagation parameter and the step of measuring said index of valvular stenosis comprises shear wave imaging.

26. The method according to claim 13, further comprising imaging the treatment region of the cardiac valve in real-time by ultrasound imaging.

27. The method according to claim 13, further comprising mechanically controlling a location of the ultrasound probe externally to the heart of the patient to keep the treatment region inside a scannable region of the ultrasound probe.

28. The method according to claim 13, wherein a motion of the treatment region comprising at least one leaflet of the cardiac valve is estimated in real-time by ultrasound imaging and the focused ultrasound waves emitted by the ultrasound probe are steered in function of said motion of the treatment region to scan the entire treatment region.

29. The method according to claim 13, wherein the duration of a pressure pulse generated by each focused ultrasound wave of the sequence of focused ultrasound waves is less than 20 microseconds.

30. The method according to claim 13, wherein each focused ultrasound wave of the sequence of focused ultrasound waves is generated by controlling at least one transducer of the ultrasound probe to emit an emission signal in a reflective cavity of the ultrasound probe, the duration of said emission signal being less than 10 milliseconds, preferably less than 1 millisecond.

31. The method according to claim 13, wherein the treatment region further comprises at least one portion of an annulus of the cardiac valve.

32. The method according to claim 13, wherein said valvular disease is valvular stenosis.

* * * * *